(12) United States Patent
Howard et al.

(10) Patent No.: US 8,176,747 B2
(45) Date of Patent: May 15, 2012

(54) TUBE PICKING MECHANISM FOR AN AUTOMATED, ULTRA-LOW TEMPERATURE STORAGE AND RETRIEVAL SYSTEM

(75) Inventors: Raymond T. Howard, Franklin, MA (US); Julian Warhurst, Hudson, NH (US); Behrouz Zandi, Lexington, MA (US); Michael A. Carman, Franklin, MA (US); James O'Toole, Franklin, MA (US)

(73) Assignee: Hamilton Storage Technologies, Inc., Hopkinton, MA (US)

( * ) Notice: Subject to any disclaimer, the term of this patent is extended or adjusted under 35 U.S.C. 154(b) by 958 days.

(21) Appl. No.: 12/184,025

(22) Filed: Jul. 31, 2008

(65) Prior Publication Data
US 2010/0028214 A1    Feb. 4, 2010

(51) Int. Cl.
*F25D 25/00*    (2006.01)

(52) U.S. Cl. ............................. 62/378; 62/337

(58) Field of Classification Search .............. 62/265, 62/337, 378, 381; 414/322
See application file for complete search history.

(56) References Cited

U.S. PATENT DOCUMENTS

| | | | |
|---|---|---|---|
| 5,735,587 | A | 4/1998 | Malin et al. |
| 6,068,437 | A | 5/2000 | Boje et al. |
| 6,129,428 | A | 10/2000 | Helwig et al. |
| 6,255,614 | B1 | 7/2001 | Yamakawa et al. |
| 6,397,620 | B1 | 6/2002 | Kelly et al. |
| 6,435,582 | B1 | 8/2002 | DaSilva et al. |

(Continued)

FOREIGN PATENT DOCUMENTS

EP    0725133 B1    12/1998
(Continued)

OTHER PUBLICATIONS

Remp, "Small-Size Store (SSS)", pp. 1-2, http://www.remp.com/index.asp?cms=22.

(Continued)

*Primary Examiner* — Melvin Jones
(74) *Attorney, Agent, or Firm* — Andrus, Sceales, Starke & Sawall, LLP

(57) ABSTRACT

A tube picking mechanism is designed for use in an automated, ultra-low temperature (e.g., −80° C.) storage and retrieval systems which stores biological or chemical samples. The samples are contained in storage tubes held in SBS footprint storage racks that are loaded into trays located within an ultra-low temperature freezer compartment (−80° C.). A tube picking mechanism resides in a tube picking chamber that is located adjacent the freezer compartment. The tube picking chamber is maintained at about −20° C. when the tube picking mechanism is in operation. The tube picking mechanism includes a cache within the tube picking chamber to facilitate fast paced shuttling of the tube racks from the freezer compartment into the tube picking chamber. The shuttle has a clamping mechanism to secure a tube rack in place when a gripper head picks a tube from the rack. The system also includes a push pin that pushes on the bottom of the respective tube as it is being picked from the tube rack. A one-dimensional bar code reader is included within the tube picking chamber. The gripper head is able to move vertically and rotate within the field of view of the one-dimensional bar code reader in order to facilitate identification and reading of one-dimensional bar codes located on the sidewall of picked storage tubes. The system also uses fans to facilitate efficient cooling of the tube picking chamber.

22 Claims, 19 Drawing Sheets

U.S. PATENT DOCUMENTS

| | | |
|---|---|---|
| 6,467,285 B2 | 10/2002 | Felder et al. |
| 6,478,524 B1 | 11/2002 | Malin |
| 6,536,859 B1 | 3/2003 | Bathe |
| 6,568,770 B2 | 5/2003 | Gonska et al. |
| 6,581,395 B2 | 6/2003 | Felder et al. |
| 6,688,123 B2 | 2/2004 | Felder et al. |
| 6,718,776 B2 | 4/2004 | Wessling et al. |
| 6,752,479 B2 | 6/2004 | Ferger et al. |
| 6,941,762 B2 | 9/2005 | Felder et al. |
| 6,990,819 B2 | 1/2006 | Darling |
| 7,013,197 B2 | 3/2006 | Melching et al. |
| 7,013,198 B2 | 3/2006 | Haas |
| 7,059,138 B2 | 6/2006 | Bonaquist et al. |
| 7,214,022 B2 | 5/2007 | Melching |
| 7,227,746 B2 | 6/2007 | Tanaka et al. |
| 7,290,396 B2 | 11/2007 | Rampersad et al. |
| 7,314,341 B2 | 1/2008 | Malin |
| 7,494,168 B1 | 2/2009 | Miller |
| 2002/0198610 A1 | 12/2002 | Malin et al. |
| 2004/0154322 A1* | 8/2004 | Felder et al. .............. 62/177 |
| 2004/0213651 A1 | 10/2004 | Malin |
| 2004/0258566 A1 | 12/2004 | Smith |
| 2005/0028538 A1 | 2/2005 | Darling |
| 2005/0069401 A1 | 3/2005 | Malin |
| 2006/0053825 A1 | 3/2006 | Owen et al. |
| 2006/0105450 A1 | 5/2006 | Owen |
| 2006/0289371 A1 | 12/2006 | Malin |
| 2007/0064383 A1 | 3/2007 | Tanaka et al. |

FOREIGN PATENT DOCUMENTS

| | | |
|---|---|---|
| EP | 1074488 B1 | 9/2002 |
| EP | 1253817 A2 | 10/2002 |
| EP | 1211197 B1 | 2/2003 |
| EP | 1441026 A1 | 7/2004 |
| EP | 1443101 A1 | 8/2004 |
| EP | 1634496 A1 | 3/2006 |
| EP | 1639892 A1 | 3/2006 |
| EP | 1721964 A1 | 11/2006 |
| EP | 1757883 A2 | 2/2007 |
| EP | 1354028 B1 | 9/2007 |
| EP | 0853657 B1 | 12/2007 |
| EP | 1477813 B1 | 2/2008 |
| WO | 98/05753 A1 | 2/1998 |
| WO | 02059251 A2 | 8/2002 |
| WO | 2006074568 A1 | 7/2006 |
| WO | 2006074569 A1 | 7/2006 |

OTHER PUBLICATIONS

Remp,"Tube Punching Module (TPM)", p. 1, http://www.remp.com/index.asp?cms=33.

RTS Life Sciences, "RTS A2—Automated Sample Management for Small Libraries/Sample Collections", pp. 1-3, http://www.rtslifescience.com/html/A2-sample-store.htm.

LiCONiC AG, "Tube Picker", p. 1, http://www.liconic.com/products/plate-management/plate-manag.html.

LiCONiC AG, "Tube Boxer", p. 1, http://www.liconic.com/products/plate-management/tube-boxer.html.

The Automation Partnership, "Polar—System Overview", pp. 1-2, http://www.automationpartnership.com/tap/sms/Polar.htm.

Matrical Bioscience, "MiniStore", pp. 1-2, http://www.matrical.com/MiniStore.php.

Nexus Biosystems, "Universal Store—Compound Storage System", pp. 1-2, http://www.nexusbio.com/Products/SampleManagement/compound_storage.php.

TTP Labtech, "comPOUND", pp. 1-2, http://www.ttplabtech.com/products/compound/index.html.

Biomicrolab, "XL20 Tube Handler", pp. 1-2, http://www.biomicrolab.com/products_XL20.htm.

Honeywell, HIH-400 Series, pp. 1-8, www.honeywell.com/sensing, Minneapolis, MN, Jan. 2007.

RTS Group, "Compound Management", http://rtslifescience.com/html/compound-management.htm, pp. 1-14, 2005.

Matrical, "MatriStore—Automated Compound Storage and Retrieval System", "MatriPress—Microwell plate storage freezer rack" http://www.matrical.com/MatriStore2.php, pp. 1-6, Spokane, WA 2007.

LiCONiC Instruments, "Product Overview", pp. 1-2, Woburn, MA, Jul. 19, 2007.

Thermo Scientific, "Automated Sample Library at -80C-Thermo Scientific", http://www.thermo.com/com/dcs/product/detail/10120038,00.html, pp. 1-2, 2007.

TECAN Group Ltd.—News, "Automated production of microfluidic devices with the Freedom EVO/REMP Small-Size Store Factory", http://www.tecan.com/page.content/index.asp?MenuID, pp. 1-2, Switzerland, 2008.

REMP, "Sample Safe", pp. 1-2, Mannedorf, Switzerland, 2007.

REMP, "Storage Family", pp. 1-6, Mannedorf, Switzerland, 2007.

Oriental Motor U.S.A. Corp., "2-Phase Stepping Motor", www.orientalmotor.com, pp. 1-2, Torrance, CA, Jan. 22, 2008.

Applied Motion Products, "Motors, Motion Control Products, Drives and Controls", http://www.applied-motion.com/products/servo/motors/NMseries.php., pp. 1-6, 2006/.

ANSI/SBS 1-2004, "Footprint Dimensions", American National Standards Institute, Society for Biomolecular Sciences, pp. 1-8, Jan. 25, 2006.

AiRTX International, "Air Knives:Aluminum 85000 Series", http://www.airtxinternational.com/catalog/82000/php., pp. 1-4, Jan. 22, 2008.

* cited by examiner

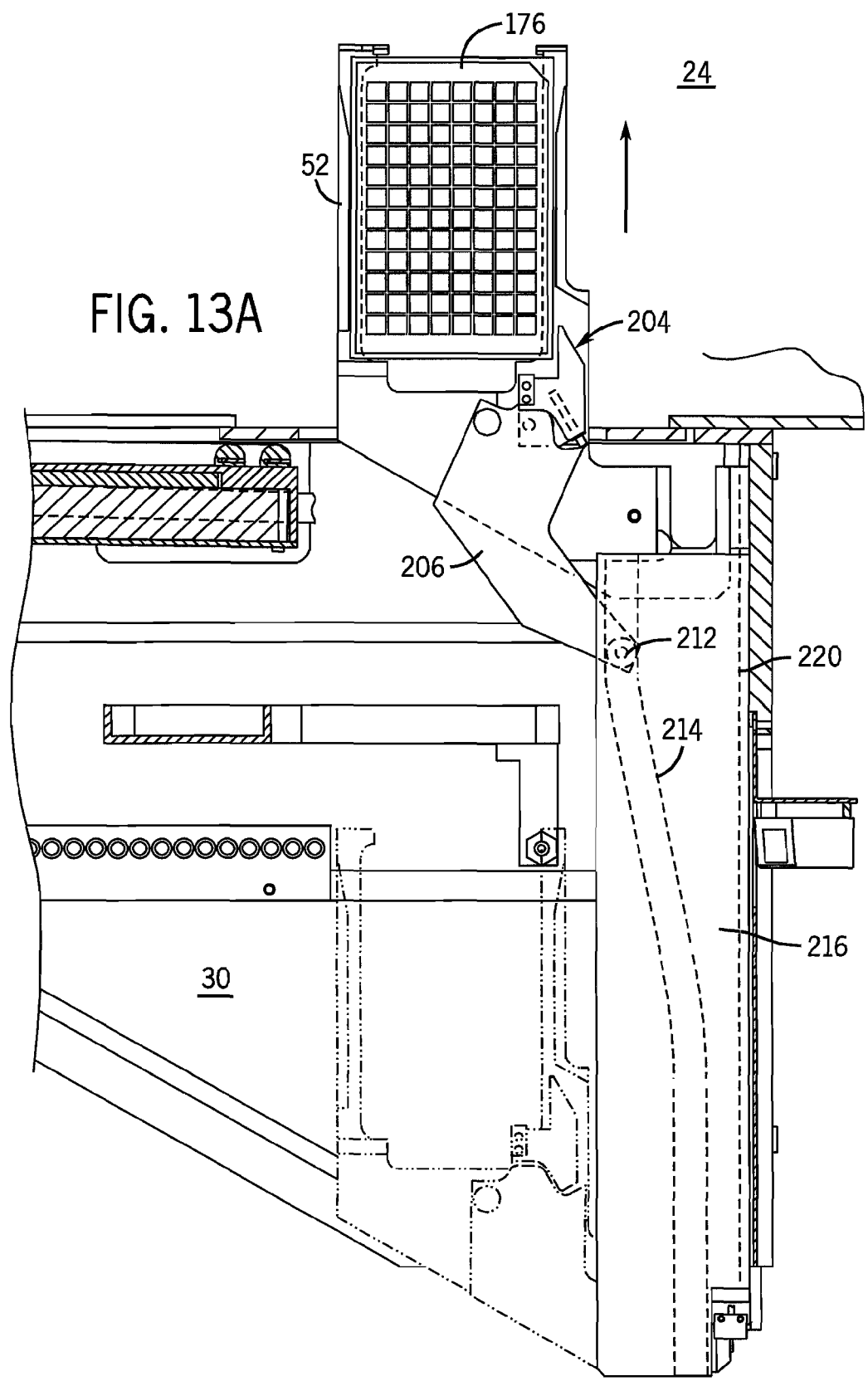

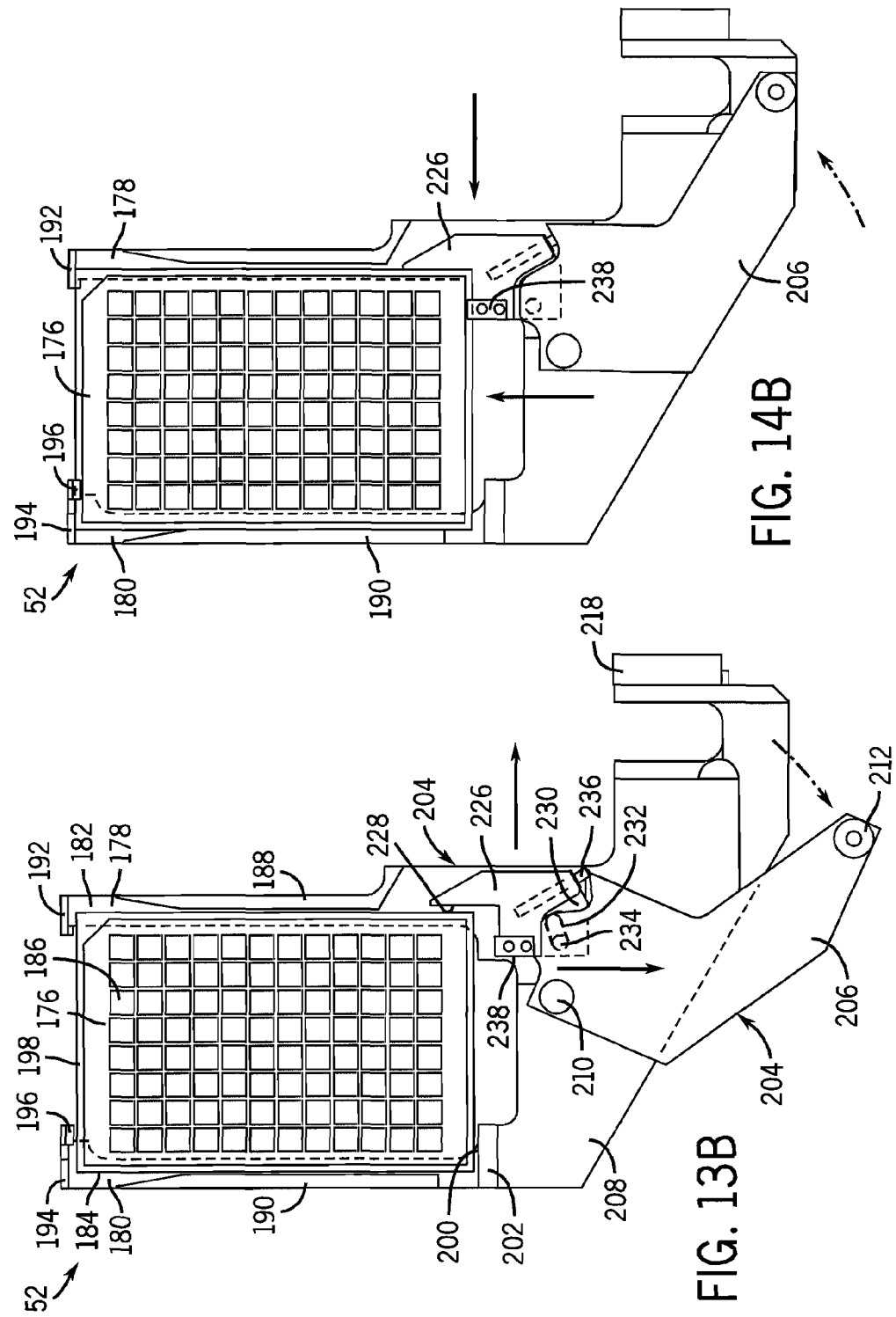

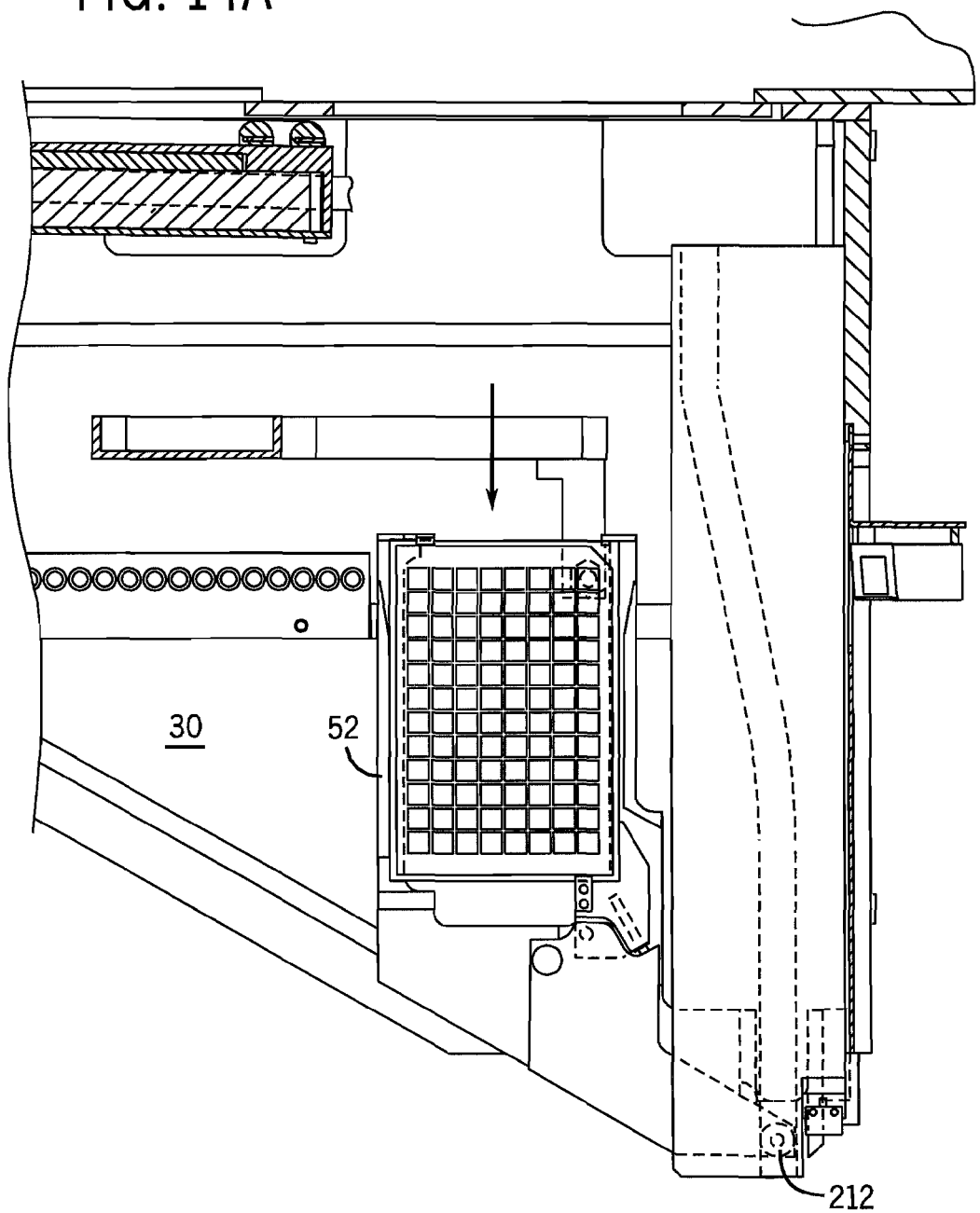

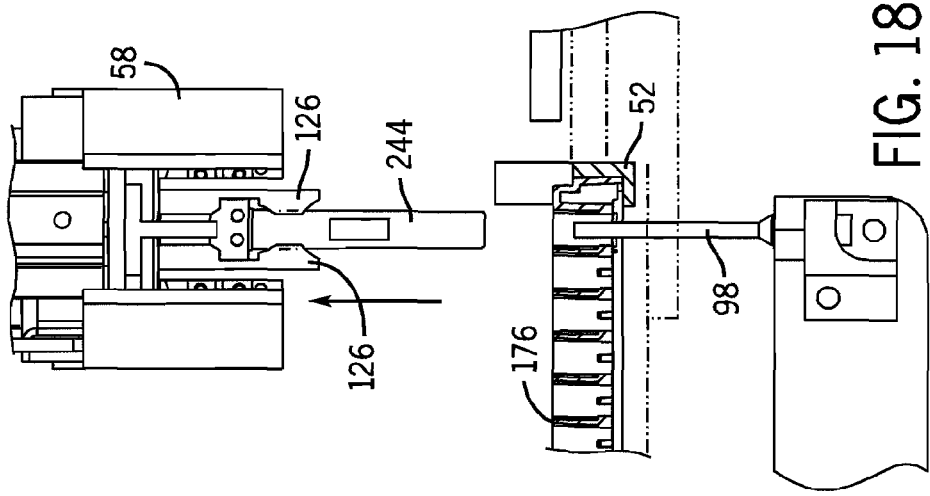
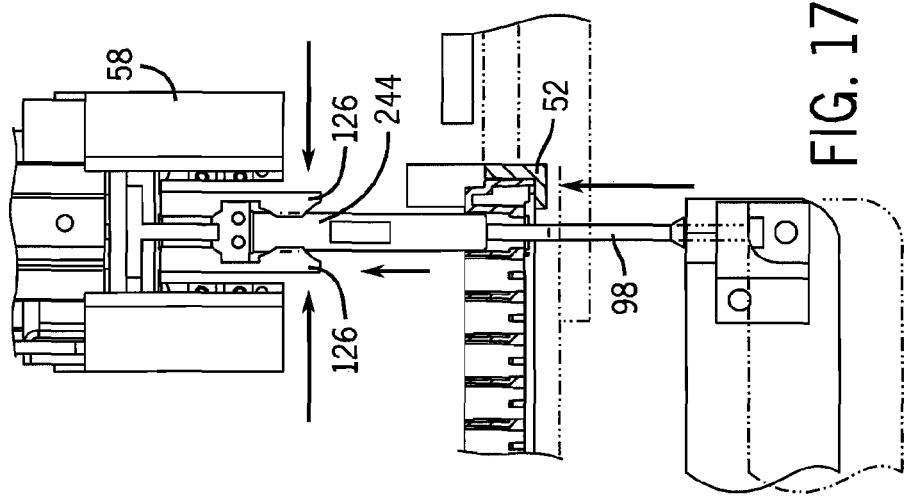
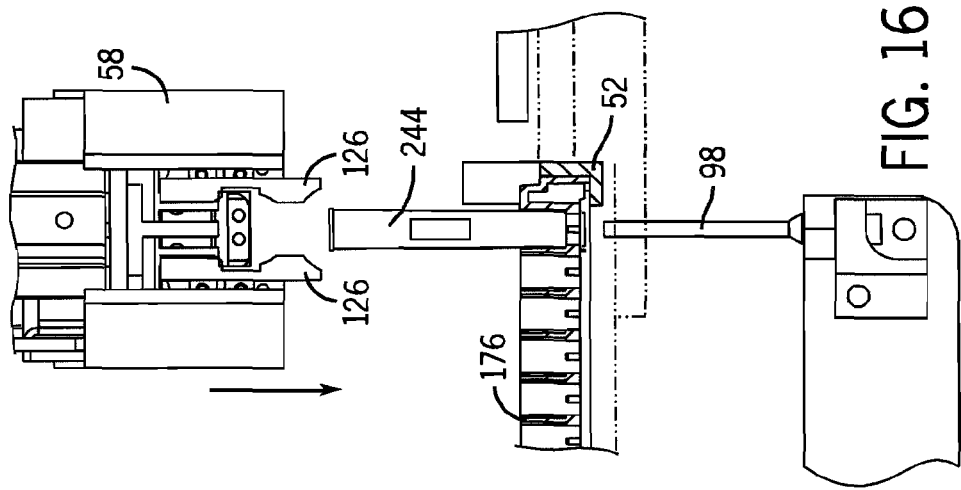

TUBE PICKING MECHANISM FOR AN AUTOMATED, ULTRA-LOW TEMPERATURE STORAGE AND RETRIEVAL SYSTEM

FIELD OF THE INVENTION

The invention is directed to features of a tube picking mechanism that is particularly well suited for use in an automated, ultra-low temperature storage and retrieval system used primarily to store biological or chemical samples.

BACKGROUND OF THE INVENTION

Storage of biological and chemical samples is becoming widespread in biotechnological and medical industries. Many of these samples must be stored at or below freezing temperatures. Generally speaking, a regular freezer operates from −5° C. to −20° C., an ultra-low temperature freezer operates from about −50° C. to about −90° C. (preferably at about −80° C.) and a cryogenic freezer operates from about −140° C. to −196° C. (the boiling point of liquid nitrogen).

The assignee of the present application has filed co-pending application Ser. No. 12/020,246 entitled "Automated Storage And Retrieval System For Storing Biological Or Chemical Samples At Ultra-Low Temperatures", by Robert P. Cloutier, Julian Warhurst, Behrouz Zandi, James O'Toole and Halvard Solbert, on Jan. 25, 2008, which is hereby incorporated by reference. This co-pending application describes an automated, ultra-low temperature sample storage and retrieval system having storage racks mounted within an insulated, ultra-low temperature freezer compartment (−80° C.). A mechanical robot is provided within the ultra-low temperature storage compartment to place sample storage containers in the storage racks and retrieve the storage containers from the racks. The sample storage containers are typically SBS footprint compatible, and normally take the form of microtiter plates, tube storage racks, reservoirs or other SBS format containers. The robot communicates with an access module in order to introduce sample storage containers into the system and retrieve the containers for use outside of the system. The freezer racks have a capacity of several hundred or more sample storage containers, such as microtiter plates or tube storage racks. The present invention is directed to a tube picking apparatus that is particularly well suited for use in the automated ultra-low temperature storage and retrieval system disclosed in the above incorporated patent application, but also may be useful in other systems as well.

As explained in the above incorporated patent application, biological samples stored in ultra-low temperature systems are often contained in sealed plastic laboratory tubes or vials having a diameter of 8 mm or larger. Larger tubes are sometimes called vials in the art, but both are referred herein as tubes or storage tubes. In any event, the tubes or vials are typically held in tube storage containers (sometimes referred to as tube racks) in arrays of, for example, 96, 48 or 24 tubes. The tube racks, as mentioned, typically have SBS footprint compatible dimensions. In some cases, a two-dimensional bar code containing identifying information is adhered to the bottom of the storage tubes and is able to be read through openings in the bottom of the SBS tube racks. The above incorporated patent application discloses the use of a two-dimensional bar code reader at the access module for this purpose. The system control system is able to keep track of the location of samples within the system based on that information. In many cases, however, two-dimensional bar codes are not adhered to the bottom of the storage tubes. In many situations, a one-dimensional bar code containing identifying information is placed manually on the sidewall of the storage tube. The variety of positions and orientations of manually placed one-dimensional bar code labels makes them difficult to read in an automated system, especially within the ultra-low temperature environment or in the access module.

As explained in the above incorporated patent application, it is not normally desirable to remove an entire SBS storage rack from the system when only one or a few storage tubes from a given rack are desired to be retrieved. The removal procedure allows for the ingress of moisture into the ultra-low temperature storage compartment, and also renders the other samples held in the same SBS tube rack susceptible to thawing, at least partially, even if the tube rack is removed from the system temporarily. The above incorporated patent application also explains that while tube picking mechanisms are generally known in the art, the environment within the ultra-low temperature freezer compartment is typically too cold to ensure reliable operation of conventional tube picking mechanisms.

In order to address these issues, the incorporated, co-pending patent application provides a tube picking chamber adjacent the freezer compartment, preferably incorporated into the insulated freezer door. A retractable shuttle door is located between the tube picking chamber and the ultra-low temperature storage compartment. A reach arm for the robot within the ultra-low temperature freezer compartment supplies a selected SBS tube rack (i.e., a source rack) to a specific location in freezer compartment that can also be accessed by a robotic shuttle constituting part of the tube picking mechanism. Picked tubes are loaded into another tube rack (i.e., a destination rack) that is intended to exit the system. The shuttle door for the tube picking chamber normally remains closed, isolating the tube picking chamber from the ultra-low temperature freezer compartment under normal storage conditions. When use of the tube picking mechanism is requested, dry gas is introduced into the tube picking chamber with the shuttle door closed in order to reduce the relative humidity within the chamber. A relative humidity sensor is located within the tube picking chamber for this purpose. When the relative humidity has been lowered to the desirable level, for example less than 2% relative humidity, the shuttle door is opened and cold air from the ultra-low temperature freezer compartment is allowed to flow into the tube picking chamber. A temperature sensor is also located in the tube picking chamber. The shuttle door is opened and closed as necessary to maintain the temperature in the tube picking chamber at a freezing temperature that is above the ultra-low temperature (−80° C.) in the storage compartment, preferably −5° C. to −25° C., e.g. about −20° C. In this manner, the tube picking mechanism, and its mechanical and electrical components, can operate in a less harsh environment which greatly improves reliability. On the other hand, by maintaining the tube picking chamber at a subfreezing temperature, the other samples in the pertinent source racks need not exit the system in order to retrieve the desired storage tube or tubes. This not only protects the other samples from premature thaw and harm, but also reduces the risk of moisture flow into the ultra-low temperature freezer compartment. Further, because the relative humidity is maintained at a low level within the tube picking compartment, tube racks can be shuttled in and out of the tube picking compartment at a relatively fast pace compared to shuttling through the main access module. Fast pace shuttling shortens exposure time outside of the −80° environment for samples not selected for retrieval.

The prior art includes tube picking mechanisms used in −20° C. freezer systems. With tube picking mechanisms for −20° C. freezer systems, it is known to use a cache for temporarily holding picked storage tubes as the tubes are being transferred between source racks and a destination rack. However, these tube picking mechanisms are typically located within the main freezer compartment, and are typically too bulky for use in the smaller-sized tube picking chamber disclosed in the above incorporated patent application. In the −80° C. system described in the incorporated co-pending patent application, it is important to keep the tube picking chamber relatively small because its existence and use is generally a burden to the cooling system.

While the system disclosed in the above-discussed incorporated patent application is designed to be used with a wide array of tube picking mechanisms, an object of the present invention is to provide a system that can efficiently and reliably shuttle tube storage racks from the ultra-low temperature storage compartment (−80° C.) into the tube picking chamber (−20° C.) at the given temperatures, as well as effectively and reliably transfer picked tubes from the retrieved source racks into a suitable destination rack designated to be exported from the system with the selected samples.

Another object of the invention, as mentioned previously, is to design a practical manner for reading one-dimensional bar codes located on the sidewall of the storage tubes.

Yet, another object of the present invention is to improve the efficiency and consistency of cooling within the tube picking chamber.

SUMMARY OF THE INVENTION

The invention is an improved tube picking mechanism that is particularly well suited for use with automated storage and retrieval systems which store biological or chemical samples in tubes held in SBS storage racks that are loaded into trays located within an ultra-low temperature freezer (−80° C.). As mentioned, the tube picking mechanism resides in a tube picking chamber maintained at about −20° C., and the tube picking chamber is preferably located in the freezer door adjacent the freezer compartment.

In one aspect of the invention, the tube picking mechanism includes a cache, having a plurality of storage tube receptacles, located within the tube picking chamber. The purpose of the cache in the tube picking chamber is to temporarily hold storage tubes picked from a variety of source racks stored in the freezer compartment in order to facilitate efficient transfer of the selected storage tubes from the system through the access module.

A retractable shuttle door separates the tube picking chamber from the ultra-low temperature freezer compartment. A shuttle for the tube picking mechanism moves between the tube picking chamber and the freezer compartment in order to shuttle tube racks one a time into the tube picking chamber and vice versa. Source racks with tubes that have been selected for extraction from the system are taken to a designated location within the freezer compartment by the freezer robot. The shuttle for the tube picking mechanism receives the source rack from the robot and transports the tube rack through the shuttle doorway into the tube picking chamber, at which time the door is closed. The shuttle preferably moves horizontally along the linear y-axis. A tube gripper head located within the tube picking chamber moves horizontally along a perpendicular x-axis, and also moves vertically along a z-axis. The tube gripper head has a pair of gripper fingers that are able to grip and lift a single tube from a receptacle in a tube rack located on the shuttle. In order to pick a selected tube from a tube rack on the shuttle, the shuttle is indexed along the y-axis and the tube gripper head assembly is indexed along the x-axis. The system also preferably includes a presenter push pin located beneath the shuttle tray. The presenter push pin remains aligned with the tube gripper head along a vertical z-axis. The push pin is moved upward to push on the bottom of the selected storage tube held in the tube rack to slightly raise (e.g., ¼ inch) the selected tube above the other tubes in the rack. Then, the tube gripper head assembly moves downward along the z-axis to allow the gripper fingers to grip the selected tube. Once the storage tube is secured, the gripper head assembly moves vertically upward to lift the tube from the receptacle in the tube rack. The tube gripper head is then moved along the x-axis to set the picked tube in one of a plurality of receptacles located in the storage tube cache within the tube picking chamber. Once the storage tube is set in the cache, the tube picking mechanism can then be used to pick another selected tube from the same source rack if desired. All picked tubes are transferred to a receptacle in the cache, at least until the cache is full. Preferably, the cache includes at least 8 receptacles. Once all of the selected storage tubes have been selected from the source rack located on the shuttle within the tube picking chamber, the shuttle door is opened and the shuttle transports the tube rack back to the designated location within the freezer compartment. The shuttle then retracts and the shuttle door closes while the freezer robot returns the source rack to its original storage location. The tube picking process repeats itself as described above until all of the selected tubes have been placed in the cache, or the cache becomes full.

Once all of the selected tubes have been placed in the cache or the cache becomes full, a "destination rack", preferably an empty tube rack, is transported to the designated location within the freezer compartment. The destination rack is intended to be filled with storage tubes for retrieval and exit from the system through the access module. The tube picking mechanism shuttles the destination rack into the tube picking chamber and loads the storage tubes from the cache into the receptacles in the rack. The tube picking mechanism then returns the destination rack to the freezer compartment. If no more storage tubes are selected for retrieval from the system, the freezer robot will pass the destination rack to the access module for extraction from the system. If additional storage tubes are selected for retrieval, the freezer robot will move the destination rack to a holding shelf within the freezer compartment. The freezer robot and the tube picking mechanism will then again coordinate to transfer selected storage tubes from tube racks in the freezer compartment into the cache in the tube picking chamber, and consequently load the tubes from the cache into the destination rack. This process is continued until all of the tubes selected for retrieval have been loaded into the destination rack or, alternatively, the destination rack becomes full, at which time the freezer robot transports the destination rack to the access module for extraction from the system.

Use of the cache within the tube picking chamber allows for relatively fast paced shuttling of the tube racks from the freezer compartment into the tube picking chamber with the same shuttling mechanism being used for both the source racks and the destination rack. Yet, exposure time outside of the −80° environment is kept at a minimum for samples not selected for retrieval. In addition, it allows for the tube picking chamber to be relatively compact because it does not require room to park a destination rack within the tube picking chamber.

In the preferred embodiment of the invention, the shuttle includes a shuttle tray which is specifically designed to hold tube racks having an SBS footprint. Often, frost within the freezer compartment can make it difficult to reliably remove storage tubes from tube racks in an automated fashion. The preferred shuttle tray therefore has a clamping mechanism to clamp the tube rack securely in place on the tray when the rack has been shuttled into the tube picking chamber. Use of the presenter push pin as described above further enhances reliability of picking tubes from frosted tube racks. As the push pin moves upward to push on the bottom of a storage tube held in a receptacle in the clamped tube rack, it facilitates release of the tube from the rack, as it lifts the tube slightly above the other tubes in the rack, prior to the gripper head lifting the tube from the receptacle in the tube rack.

The shuttle tray preferably includes a z-axis clamp which prevents the tube rack from moving upward when the presenter push pin pushes upward on the bottom of the respective storage tube and the gripper head grabs the storage tube and lifts the storage tube from the receptacle on the tube rack. In addition, the shuttle tray includes a back stop to limit y-axis movement of the rack placement on the shuttle tray when the shuttle tray picks up the tube rack from the freezer compartment. The shuttle tray also has a pair of arms extending generally in the y-axis direction with vertical walls extending up from the arms to limit x-axis movement. The z-axis clamp is preferably located at a distal end of one of the arms, and a clamping mechanism is preferably located at a proximal end of the other arm. The preferred clamping mechanism pushes the tube rack into engagement with the z-axis clamp and the vertical wall on the other arm in order to clamp the tube rack in place. Preferably, the clamping mechanism is driven by a cammed following device which opens the clamp when the shuttle tray is transported into the freezer compartment and closes the clamping mechanism when the shuttle tray is located within the tube picking chamber.

In another aspect of the invention, a one-dimensional bar code reader is located within the tube picking chamber in order to identify and read one-dimensional bar codes located on the sidewall of storage tubes picked and lifted from source racks within the tube picking chamber. To facilitate locating and reading the bar codes on the sidewall of storage tubes, the gripping head is designed to move vertically along a z-axis, and also rotate about the z-axis. As mentioned, the preferred gripper head assembly can also move horizontally along an x-axis, but it does not move in the preferred embodiment along the y-axis. The one-dimensional bar code reader is, therefore, preferably located at the y-axis location for the gripper head. In operation, the gripper head lifts the respective tube from the tube storage rack in the tube picking chamber, and presents the tube within the field of view of the one-dimensional bar code reader. If necessary, the gripper head moves the tube vertically and rotates the tube so that a bar code on the sidewall of the tube falls within the field of view of the one-dimensional bar code reader.

Preferably, the gripper head has a pair of gripper head fingers and a shucker as is known in the art. A bearing mechanism, preferably a V-groove bearing mechanism, rotatably mounts the gripper head to a carriage head. A motor and belt rotates the gripper head about the z-axis with respect to the carriage head assembly. A z-axis linear drive mechanism moves the carriage head, as well as the gripper head, vertically along the z-axis. The gripper head fingers and the shucker on the gripper head are preferably pneumatically powered, and the mounting mechanism for the rotatable gripper head to the carriage head preferably allows for the air supply tubing to wrap around the gripper head or unwrap as the gripper head is rotated.

The carriage head is mounted for z-axis vertical movement to a z-axis plate. The z-axis plate, in turn, is mounted to the frame of the tube picking chamber via an x-axis linear drive mechanism which moves the z-axis plate horizontally along an x-axis. As mentioned, x-axis movement is necessary to transport storage tubes from tube racks (and from within the field of view for the one-dimensional bar code reader) to the cache within the tube picking chamber, and vice versa.

With a one-dimensional bar code reader in the tube picking chamber, the system can be used to take inventory of storage tubes entered into the system through the access module which are identified by a one-dimensional bar code on the sidewall of the storage tube, rather than a two-dimensional bar code on the bottom of the storage tube. The system can also be used to confirm storage tube identity when retrieving selected storage tubes from the system, if a one-dimensional bar code is present on the sidewall of the respective storage tube.

As mentioned, it is preferred that the tube picking mechanism resides in a tube picking chamber maintained at about −20° C., and that the tube picking chamber be located adjacent the ultra-low temperature freezer compartment. In accordance with another aspect of the invention, fans are used within the tube picking chamber in order to improve the efficiency and consistency of cooling within the tube picking chamber. In this aspect, the method begins when a signal is received to prepare the tube picking chamber prior to using the tube picking mechanism such that the chamber is cooled to the appropriate temperature, (e.g. −20° C.), before use. Once the signal to prepare is received, a first fan begins to circulate air throughout the tube picking chamber. This fan operates continuously until the tube picking session has been terminated. It has been found that constant circulation of air is important to maintain a consistent temperature throughout the chamber. If necessary, dry gas is introduced into the tube picking chamber in order to reduce the relative humidity to the desired level, for example, less than 2% relative humidity. Once it is determined that the relative humidity is at the appropriate level, the door is opened between the tube picking chamber and the freezer compartment in order to allow ultra-low temperature air from the freezer compartment into the tube picking chamber. A second fan blows air from the tube picking chamber through the open door into the freezer compartment for the initial cool down. It has been found that the use of the second fan greatly improves the speed of cooling the tube picking chamber to the desired predetermined temperature (e.g., −20° C.). Once this temperature is reached, the door is closed, unless the shuttle needs to move between the tube picking chamber and the freezer compartment, or vice versa. The second fan is turned off at this point; however, the first fan remains on to continue circulating air throughout the tube picking chamber. If the temperature within the tube picking chamber rises above a second predetermined temperature (e.g. −15° C.), the door is opened (or partially opened) until the temperature within the tube picking chamber cools to the first predetermined temperature. This process is repeated as necessary.

It is believed that the invention resides not only in the combination of various system components as described herein, but also in the manner in which the above described components are used in order to provide the stated objects of the invention. Also, as mentioned, the invention is particularly well suited for use with the automated, ultra-low temperature storage and retrieval system disclosed in the above incorporated co-pending patent application, but certain aspects can also be used in other applications as well such as in a main freezer compartment in a −20° C. system.

The foregoing and other aspects, objects, features and advantages of the invention will be apparent to those skilled in the art from the following drawings and description of the preferred embodiment of the invention.

BRIEF DESCRIPTION OF THE DRAWINGS

FIG. 10 depicts the shuttle door in a closed position.

FIG. 13A is a downward looking schematic drawing illustrating the shuttle tray in a fully extended position within the freezer compartment.

FIG. 13B is a detailed view illustrating the position of a shuttle clamping mechanism when the shuttle mechanism is located in the fully extended position shown in FIG. 13A.

FIG. 14A is a view similar to FIG. 13A in which the shuttle tray is in a fully retracted position within the tube picking chamber.

FIG. 14B is a detailed view illustrating the position of the shuttle clamping mechanism when the shuttle tray is in the fully retracted position shown in FIG. 14A.

FIGS. 16, 17 and 18 are schematic drawings illustrating the steps taken when the gripper mechanism picks a tube from a tube rack.

DETAILED DESCRIPTION OF THE DRAWINGS

Figure 1:
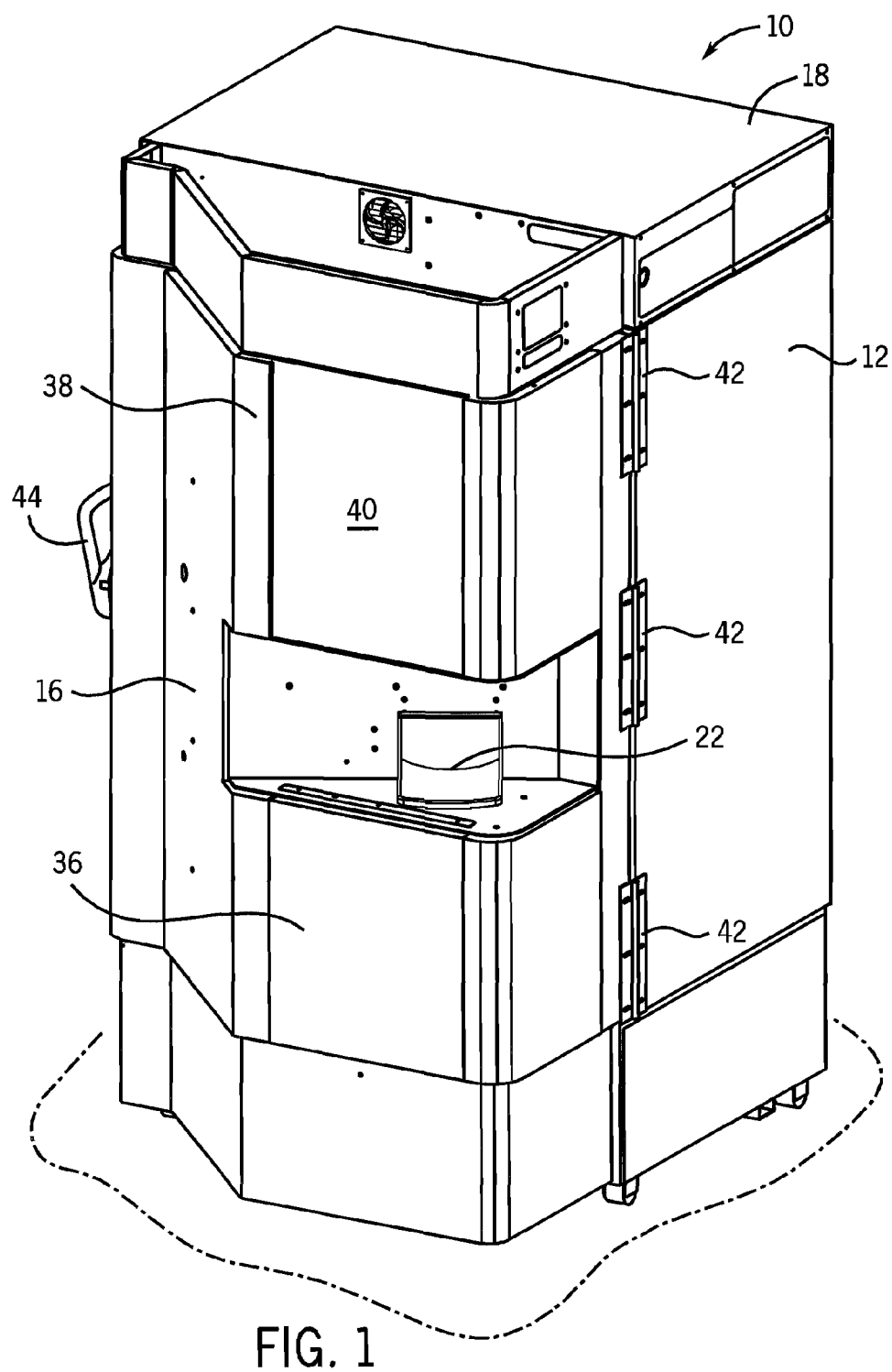
FIG. 1 is a perspective view of an automated, ultra-low temperature storage and retrieval system including a tube picking mechanism constructed in accordance with the preferred embodiment of the invention.
Figure 2:
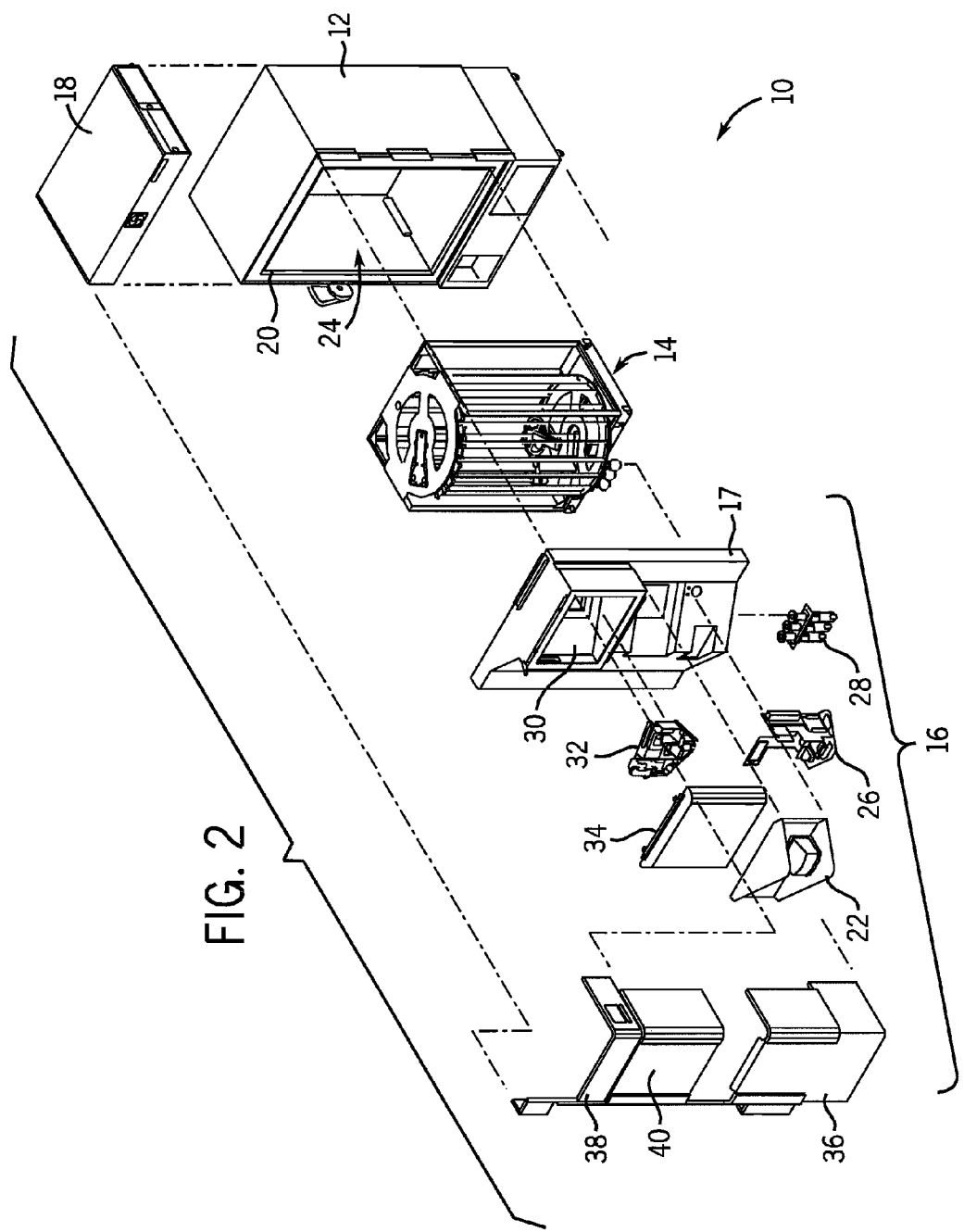
FIG. 2 is an exploded view of the ultra-low temperature, automated storage and retrieval system shown in FIG. 1.

The Figures illustrate various aspects of the preferred embodiment of the invention. FIGS. 1 and 2, in particular, show an automated storage and retrieval system 10 configured to store sample storage containers such as racks for holding sealed storage tubes at ultra low temperatures (e.g. −80° C.), as disclosed in co-pending incorporated application Ser. No. 12/020,246. As mentioned, a tube picking mechanism 32 constructed in accordance with the present invention is particularly well suited for use with the automated, ultra-low temperature storage and retrieval system 10 shown and described in the co-pending incorporated '246 patent application, although various aspects of the invention can be used in connection with other systems.

When the system 10 incorporates a tube picking mechanism 32 is normally designed to store SBS footprint compatible tube racks having tubes or vials of a single size. For example, the system 10 will be used to store tube racks containing arrays of 8 mm storage tubes, or tube racks containing arrays of 16 mm vials. The system 10 generally includes a freezer body 12, an internal storage rack and robot mechanism 14, a custom insulated door 16, and an electrical box 18. The preferred freezer body is an upright −80° C. freezer body, purchased from Thermo-Scientific, the Forma 907 series, which is designed for ultra-low temperature storage for pharmaceutical, biotech, and blood bank applications. More details of the preferred freezer body are disclosed in the co-pending incorporated '246 patent application. Other standard freezers capable of cooling to −80° C. may be suitable as well.

As mentioned in the co-pending incorporated '246 patent application, the insulated custom door 16 includes an insulated panel 17 and several other components. The door 16 includes an access module 22 in which sample storage containers, such as tube racks, are placed in order for transfer into the storage shelves in the freezer compartment 24. An electrical control and pneumatic package 26 is also mounted to the insulated door 16 as are servomotors 28 and magnetic couplers for driving the robot 48, FIG. 3. The insulated door 16 also includes a tube picking chamber 30 in which a tube picking mechanism 32 resides. An inside cover 34 having a window is permanently mounted to the outside of the insulated door panel 17 in order to enclose the tube picking chamber 30. Decorative covers 36, 38 are mounted to the front of the insulated door panel 17. An upper decorative cover 38 has a window 40, preferably made of smoke polycarbonate, to allow viewing of the tube picking mechanism 32 through the window on the inside of the cover 34. As further mentioned in the co-pending incorporated '246 patent application, the box 18 on the top of the freezer body 12 preferably houses an electronic controller, power distribution electronics, battery and also includes an inlet port from a compressed dry gas source (not shown). The insulated front door 16 is mounted to the freezer body using hinges 42, and a latch 44 as is known in the art. Although not shown in the Figures, the system 10 would include a monitor and user interface as is known in the art, such as used in connection with the TekCel TC™ biological storage unit, or the Hamilton Storage Technologies Tube-Stor™.

Figure 3:
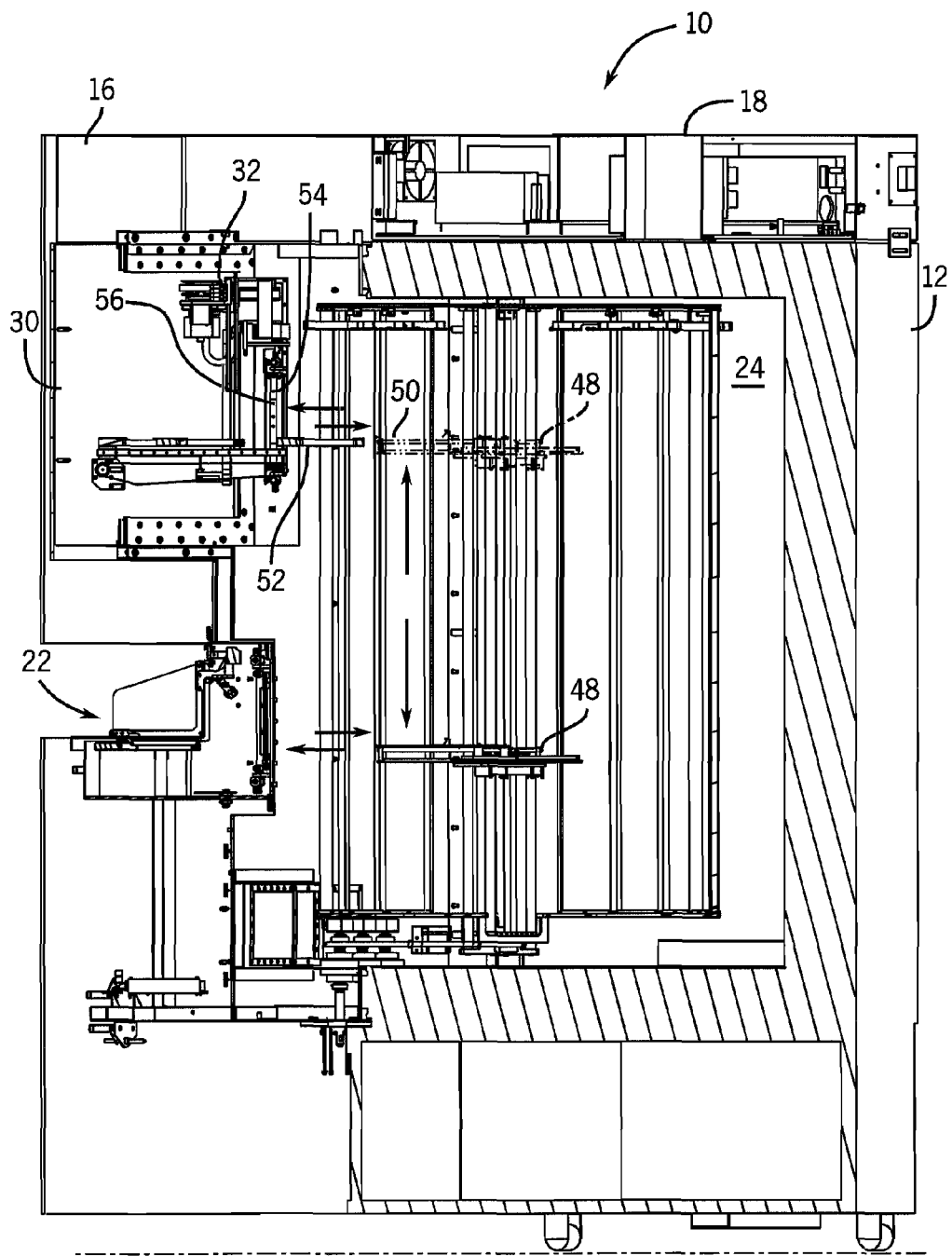
FIG. 3 is a schematic view illustrating operation of a robot within the freezer compartment and a tube picking mechanism located within a tube picking chamber in the system shown in FIGS. 1 and 2.

Referring now to FIG. 3, the preferred custom insulated door 16 includes a chamber 30 for holding the tube picking mechanism 32. The robot 48 within the freezer compartment 24 can be instructed to bring a tube rack containing sealed storage tubes of biological or chemical samples to a designated location 50 within the freezer compartment 24. The designated location 50 is accessible by both the robot 48 in the freezer compartment and a shuttle 52 for the tube picking mechanism 32. The tube picking compartment 30 includes a doorway 56 that provides access between the tube picking chamber 30 and the freezer compartment 24 and vice versa. A door 54, which is controlled by a pneumatically controlled mechanism, opens and closes to provide access. In FIG. 3, the door 54 is in the open position for shuttling tube racks in and out of the tube picking chamber 30. Within the freezer compartment 24, the system 10 will typically contain shelves for more than several hundred or more tube racks. When the system 10 is programmed to retrieve tubes from the various source racks, the source racks are fed to the designated location 50 by the robot 48 one at a time. The shuttle tray 52 for the tube picking mechanism 32 receives the chosen source rack at the designated location and transports the source rack into the tube picking chamber 30, at which time the tube picking mechanism 32 picks the selected tubes from the source rack. As described in more detail below, the picked storage tubes are temporarily stored in a cache 82, FIG. 4, located within the tube picking chamber 30. When all the tubes have been picked from the chosen source rack, the shuttle mechanism 52 returns the source rack to the designated location 50, and the robot 48 then returns the source rack to its home location in the freezer compartment. The robot 48 then retrieves the next chosen source rack and transports it to the designated location 50. This source rack 50 is then shuttled into the tube picking chamber 30 for tube picking as described above. The process is repeated until all the storage tubes of interest have been picked from the respective source racks by the tube picking mechanism 32, or the cache 82 becomes full. At that point, a destination rack, which is preferably an empty tube rack, is placed on the shuttle tray 52 by the robot 48 at the designated location 50 in the freezer compartment 24. The destination rack is then shuttled into the tube picking chamber 30 by the tube picking mechanism 32 and storage tubes are loaded from the cache 82 into the destination rack. If it is desired to extract more tubes from the system 10, one or more additional source racks and the destination rack are shuttled into the tube picking chamber 30 as necessary. When the destination rack is full, or all of the selected tubes have been loaded into the destination rack, the destination rack is shuttled to the designated location 50 in the freezer compartment 44. From there, the robot 48 transports the destination rack to the access module 22 for extraction from the system, as described in the co-pending '246 patent application.

Figure 4:
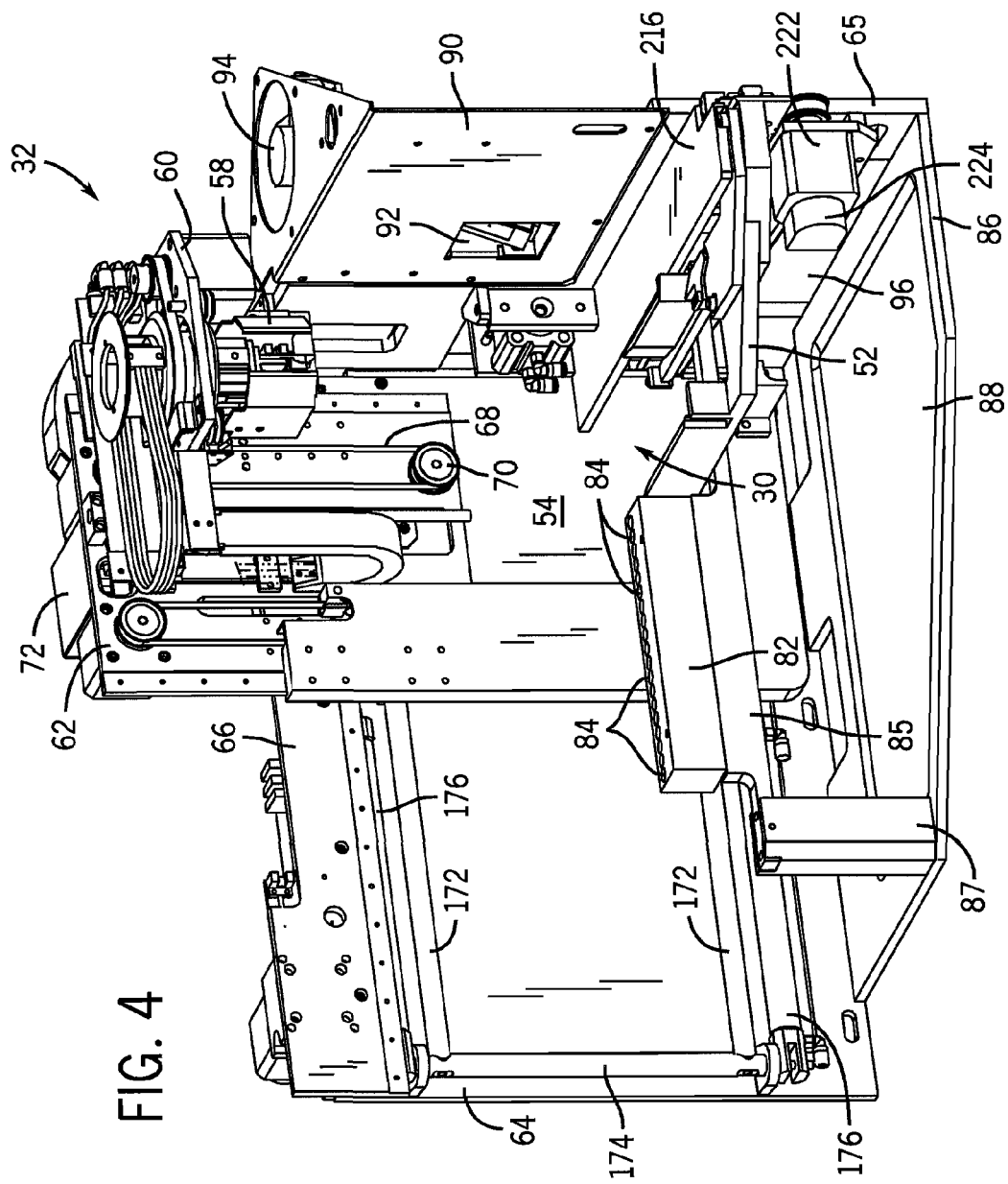
FIG. 4 is a perspective view of a tube picking mechanism constructed in accordance with a preferred embodiment of the invention.

FIG. 4 shows the internal components of a tube picking mechanism 32 constructed in accordance with a preferred embodiment of the invention. The tube picking mechanism 32 includes a shuttled tray 52 which moves linearly along a y-axis. The door 54 must be opened in order for the shuttle 52 to move into the freezer compartment 24. The operation of the shuttle 52 is described below in detail with respect to FIGS. 13A, 13B, 14A and 14B.

The tube picking mechanism 32 also includes, in accordance with the preferred embodiment of the invention, a rotatable gripper head 58. The specific components of the rotatable gripper head 58 are described in more detail with respect to FIGS. 7-9. Briefly, the gripper head 58 is mounted for rotation to a carriage head 60. The carriage head 60 is mounted to a z-axis plate 62. The z-axis plate 62 is in turn mounted to the frame 64 of the tube picking mechanism 32 via an x-axis linear drive mechanism 66. The z-axis plate 62 is therefore movable along an x-axis axis, which is perpendicular to the y-axis. On the other hand, the gripper head 58 is movable vertically along a z-axis. The carriage head 60 is attached to a z-axis bearing 76, see FIG. 5. The z-axis bearing 76 is guided for vertical movement along rail 78. The carriage head 60 (to the rotatable gripper head 58 is attached) is clamped to a belt 68 which is driven via a stepper motor 72 and toothed pulley 70 in order to move the gripper assembly 60 (and the gripper head 58) vertically along the z-axis. The drive belt 68 is preferably a small-pitch timing belt made of a material suitable for low temperature operation. A counterweight 74 is preferably attached to the belt 68 so that the gripper assembly 58 rests in an up position when there is no power to the system 10. The counterweight 74 is mounted along a vertical guide 75. An optical sensor 80 senses when the z-axis bearing 76 is in the home position.

Referring still to FIG. 4, a cache 82 having a plurality of storage tube receptacles 84 is located, in accordance with the preferred embodiment of the invention, within the tube picking chamber 30. The purpose of the cache 82 is to temporarily store picked tubes within the tube picking chamber 30 until an appropriate time for loading the picked tubes into a destination rack for extraction from the system. It is preferred that the cache 82 contain at least eight storage tube receptacles 84 in order to best facilitate system throughput. However, the number of receptacles 84 will typically vary with the size of storage tube for which the system 10 is designed. For example, if the system 10 is designed to hold 8 mm tubes, the cache 82 may include as many as eighteen (18) receptacles or more. On the other hand, if the system 10 is designed to hold racks of 16 mm vials, the cache 82 might include as few as eight (8) receptacles. The receptacles 84 in the cache 82 are aligned linearly along the fixed y-axis position for the gripper head 58. The cache 82 is mounted to a horizontal support beam 85 that is mounted at one end to the frame 65 and at the other end to an upstanding pedestal 87. To pick a tube, the shuttle mechanism 52 is indexed along the y-axis within the tube picking chamber 30 in order to align a tube storage rack on the shuttle 52 in the appropriate y-axis position for the gripper head 58. The z-axis plate 62 moves the gripper head 58 in the x-axis direction to hover over a selected storage tube in the rack on the shuttle 52. The gripper head 58 then picks the selected tube from the rack on the shuttle 52. Once the selected tube is picked from the rack, the z-axis plate 62 is moved in the x-direction to a position over one of the respective receptacles 84 in the cache 82, and the picked tube is set into the receptacle 82 in the cache 82.

The frame 64 for the tube picking mechanism 32 includes a bottom plate 86 which includes a depressed bed pan area 88. The bottom plate 86 is attached to both vertical walls 64, 65 of the frame and provides structural support for the frame 64, 65. The recessed bed pan area 88 in the bottom plate 86 catches leaks and facilitates clean up. This is helpful because, in many cases, the samples can be hazardous.

A sidewall 90 is mounted to vertical frame member 65. The sidewall 90 includes a window for a one dimensional barcode reader 92, such as a DC-powered reader from Keyence. The one dimensional bar code reader 92 is mounted to the wall 90 so that its field of view extends through the window into the tube picking chamber 30. A circulation fan 94 is also mounted to the sidewall 90. The circulation fan 94 moves air downward and through an opening 96 underneath the shuttle 52 into the tube picking chamber 30.

Figure 5:
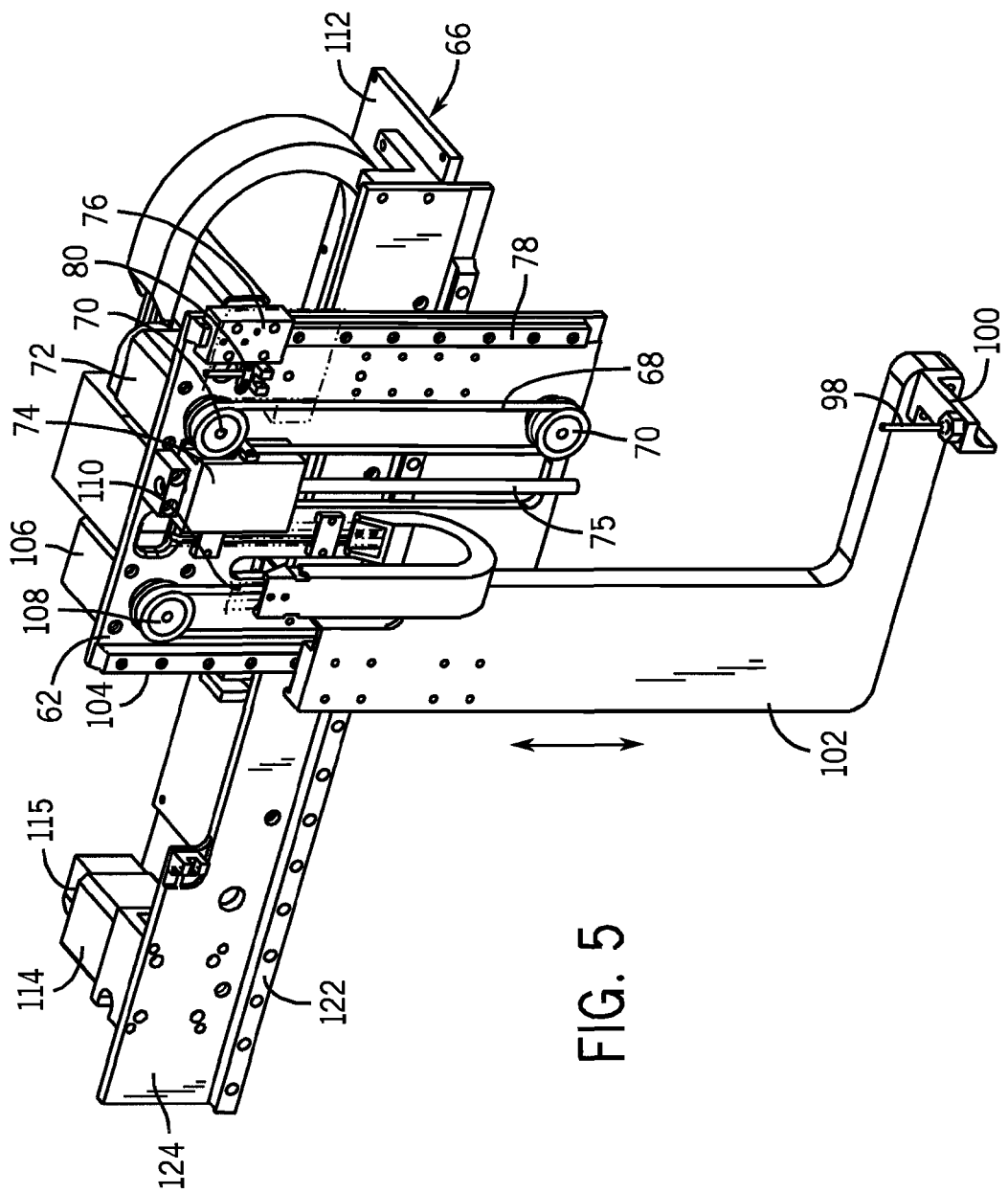
FIG. 5 is a front perspective view of various components of the tube picking mechanism constructed in accordance with the preferred embodiment of the invention, namely a z-axis plate and a presenter push pin.
Figure 6:
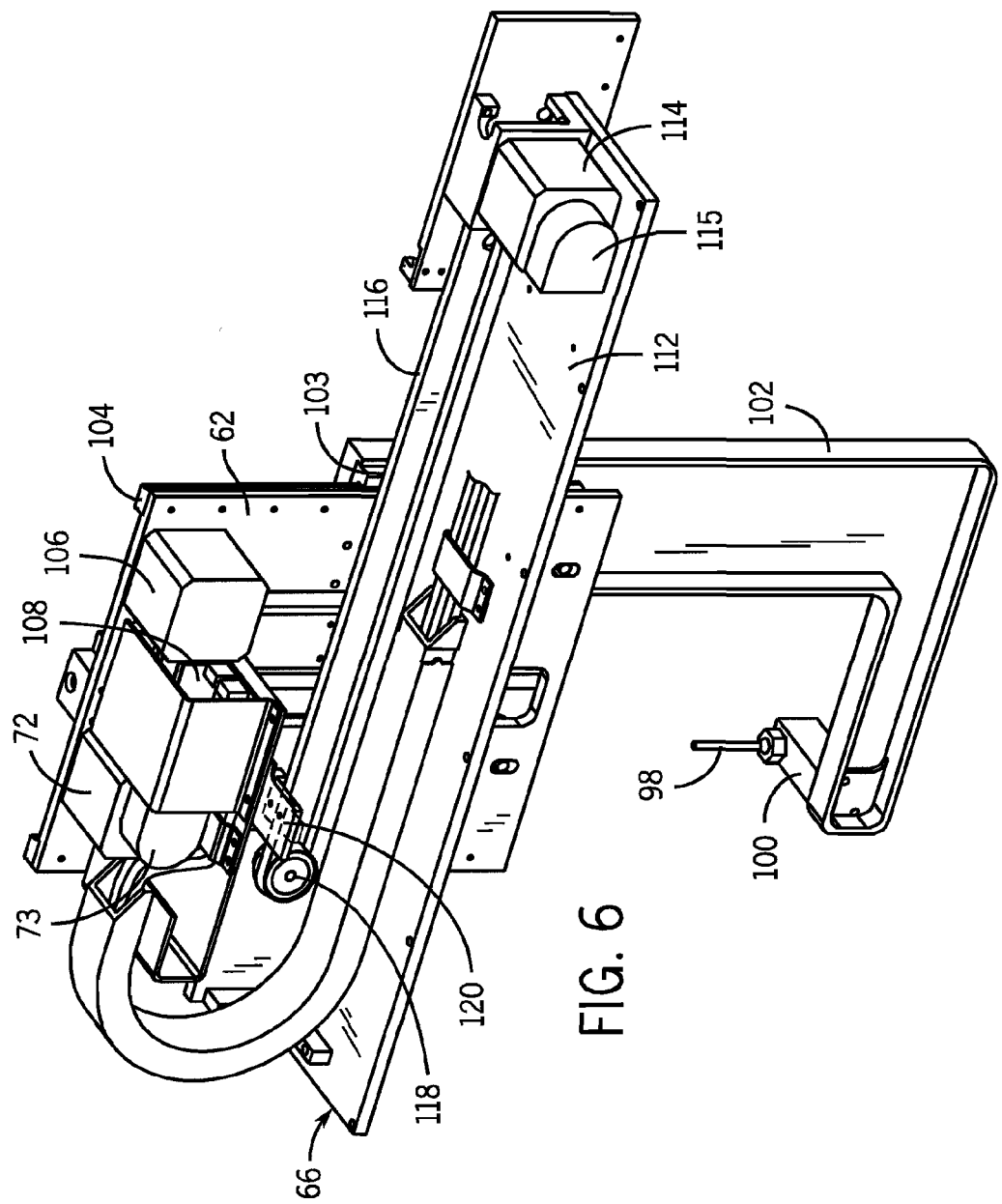
FIG. 6 is a rear perspective view of the components shown in FIG. 5.

Referring now to FIGS. 5 and 6, the z-axis plate 62 includes not only a vertical drive for the gripper head 58, 60 but also a vertical drive for a presenter push pin 98. The presenter push pin 98 moves along the x-axis with the z-axis plate 62 such that it remains aligned along the z-axis of the gripper head assembly 58. The presenter push pin 98 is mounted via mounting bracket 100 attached to the end of an L-shaped presenter arm 102. The presenter arm 102 is mounted via a linear bearing 103 to vertical rail 104. A stepper motor 106 mounted to the z-axis plate 62 drives a pulley 108 and belt 110. The belt 110 as with belt 68 is preferable a small-pitch timing belt made of a material suitable for low temperature operation. The presenter arm 102 is clamped to the belt 110 such that operation of the stepper motor 106 causes the presenter push pin 98 to move along the z-axis for the gripper head 58. The stepper motor 106 for the presenter arm 102 does not require an encoder because it will naturally fall to its home position in case the system looses power. Note that the motion of the presenter arm 102 along the z-axis can be moved independently of the z-axis motion for the gripper head 58, 60. The stepper motor 72 for the z-axis movement of the gripper head 58, 60 has an encoder 73 which monitors the number of revolutions of the output shaft of the stepper motor 72 in order to provide this information to the control system. A circuit board 108 is attached to the z-axis plate 62 between motors 106 and 72.

As mentioned, the z-axis plate moves along an x-axis. The x-axis linear drive plate 66 is mounted at one end to vertical frame wall 64 and at the other end to the perpendicular vertical frame wall 65. A linear bearing rail 122 is mounted on the drive plate 66. The z-axis plate 62 has two linear bearing blocks attached to its back side (not shown) which are mounted to rail 122. An x-axis stepper motor 114 and encoder 115 along with a belt 116 and pulley 118 drive are mounted to the x-axis linear drive plate 66 as a horizontal plate 112 attached to the drive plate 66. The driven pulley for the x-axis drive is not visible in the figures, although the idler pulley 118 is visible in FIG. 6. As also shown in FIG. 6, belt clamp 120 is mounted to the z-axis plate 62 and clamps the belt 116 such that the x-axis stepper motor 114 drives belt 116 in order to adjust the position of the z-axis plate 62 along the x-axis. As is known in the art, optical sensors and flags are used in order to monitor the home position and fully extended position for the z-axis plate 62 along the x-axis. Although not shown clearly in the drawings, a temperature sensor and an RH sensor are preferably mounted to the horizontal plate 112 as well.

Figure 7:
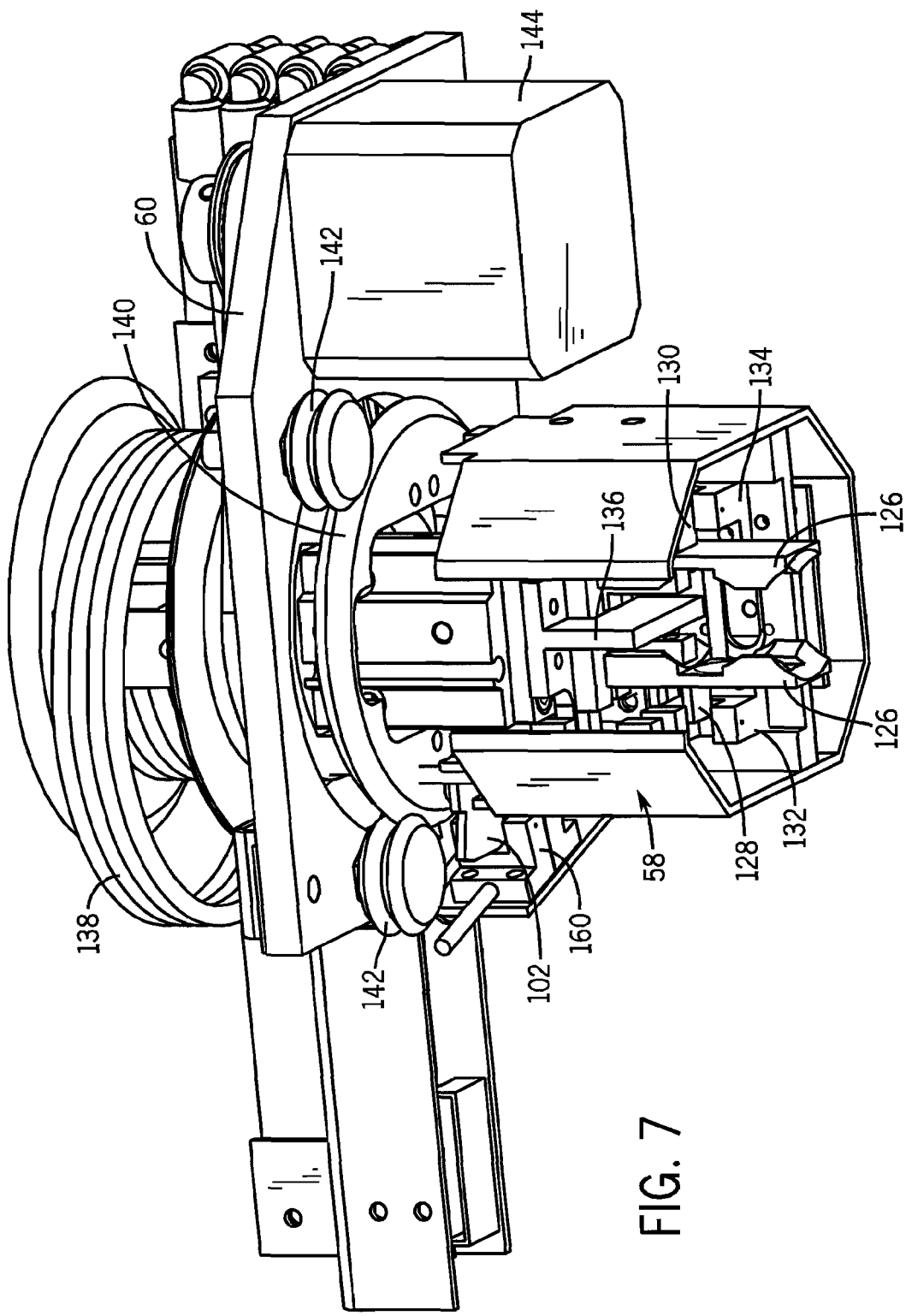
FIG. 7 a lower perspective view of a rotatable gripper head constructed in accordance the preferred embodiment of the invention.

FIG. 7 shows the gripper head 58 attached to a carriage head 60. Note that the structure of the gripper head 58 in many respects is similar to gripper heads used in previous picker systems, however, in accordance with the invention, the gripper head 58 is mounted to the carriage head 60 to rotate about the z-axis. The gripper head assembly includes gripper fingers 126 which form a gripper jaw that can be opened and closed. As is known in the art, the gripper fingers 126 are preferably formed in order to form four gripping pads that are spaced around the circumference of the picked tube, preferably as close to evenly spaced as possible. Even spacing is typically easier to accomplish for gripping fingers 126 designed for use with smaller storage tubes such as 8 mm tubes, but more difficult with gripping fingers 126 designed for larger tubes such as 16 mm vials. The gripper fingers 126 shown in FIG. 7 are made of machined aluminum and are designed for picking 16 mm vials. Preferably, the gripper fingers 126 include flags 128, 130 which interact with optical sensors 132, 134 respectively. Optical sensor 132 is mounted farther away from the gripper finger 126 than optical sensor 134. The purpose of the flags 128, 130 and the sensors 132, 134 is to monitor the state of the gripping fingers 126. When the gripping fingers 126 are in their fully opened position, both flags 128, 130 trip the respective sensors 132, 134 and both sensors 132,134 provide an "on" signal. When the gripper fingers 126 are clamped around a vial or tube, flag 128 moves out of interference thereby turning off the left sensor 132. On the other hand, the flag 130, which is longer than the flag 128, continues to block sensor 134 and the sensor remains in the on position 134. This intermediate position thus indicates that a tube or vial is present between the gripper fingers 126. In case there is misfire, the gripper fingers 126 will close fully against one another. In this case, both flags 128, 130 move inward out of interference with both sensors 132, 134 thereby registering both sensors 132, 134 in an off position.

FIG. 7 also shows a shucker 36 which moves vertically up and down to facilitate removal of a picked storage tube or vial from the fingers 126 when the fingers 126 are released. The operation of the gripper fingers 126 and the shucker 132 is controlled pneumatically by air pressure provided through tubes 138.

The gripper head 58 is mounted to a disc shaped v-guide 140. The disc shaped v-guide 140 is mounted to a set of v-guide rollers 142, preferably three v-guide rollers 142 mounted 120° apart from one another. The v-guide rollers 142 are mounted to the carriage head 60, for example using a threaded screw and bolt. A motor 144, preferably without an encoder, is mounted to the underside of the carriage head 60. The purpose of the motor 144 is to power a pulley and belt mechanism which drives rotation of the gripper head 58, preferably for range of rotation of about 350°.

Figure 8:
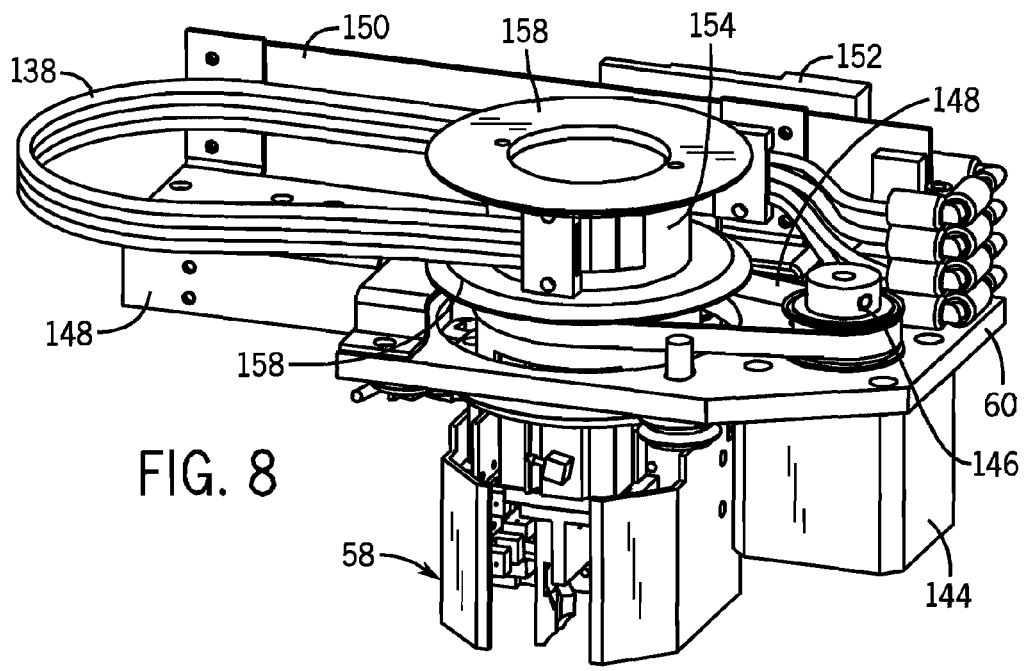
FIGS. 8 and 9 are perspective views illustrating the wrapping and unwrapping of air pressure hoses as the gripper head rotates.
Figure 9:
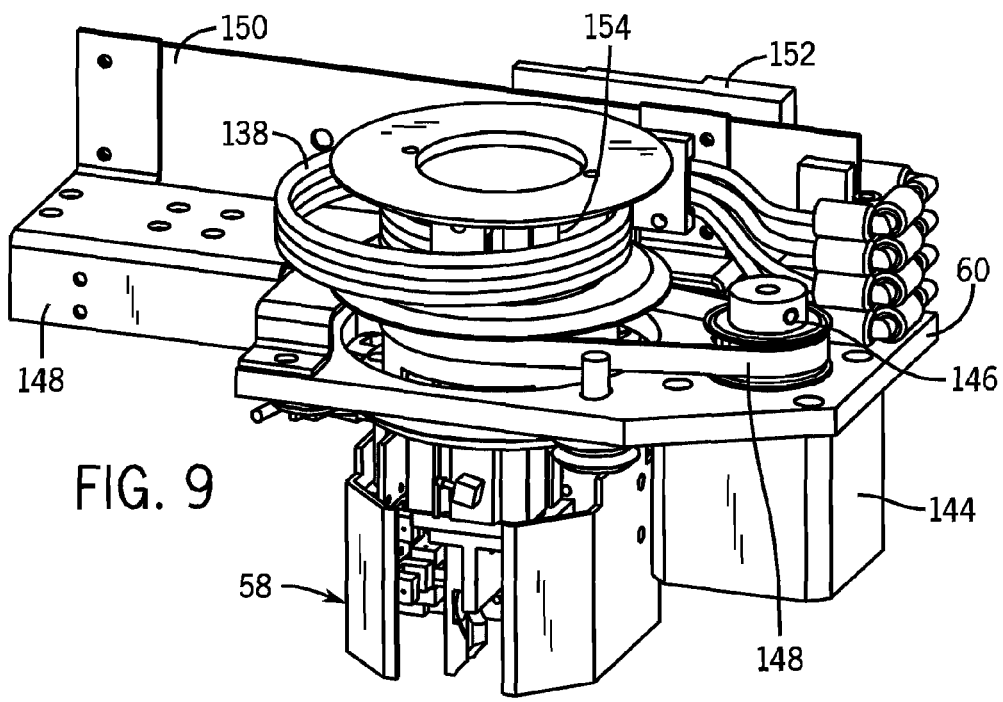

Referring now to FIGS. 8 and 9, the motor 144 drives timing pulley 146 mounted to the top surface of the carriage head 60. Cold temperature belt 148 wraps around the body of the gripper assembly 58 and the stepper pulley 146. As mentioned, air pressure hoses 138 are used to control the operation of the gripper fingers 126 and the shucker 136. A tray 148 is attached to the carriage head 146, primarily for the purpose of supporting the air hoses 138 when the hoses 138 are in a fully extended position as shown in FIG. 8. A circuit board 150 is also mounted to the carriage head 60. The carriage head 60 includes a rear vertical wall 152 which is mounted to the z-axis plate 62 shown for example in FIG. 5. FIG. 8 illustrates the gripper head 58 being rotated to its home position in which the air pressure hoses 138 are fully extended. On the other hand, FIG. 9 shows the air pressure lines 138 being wrapped around the body 154 of the gripper head 58 after the gripper head 58 rotated. Disc shaped guides 158 are mounted to the gripper head 58 in order to facilitate alignment of the air pressure hoses 138 when wrapping or unwrapping as the gripper head 58 rotates. Referring again, briefly to FIG. 7, an optical sensor 160 senses the position of flag 162 in order to determine whether the gripper head 58 is in its rotational home position. The sensor 162 is mounted to a bracket that is mounted to the carriage head 60 whereas the flag 162 is mounted to the rotating gripper head 58.

Figure 10:
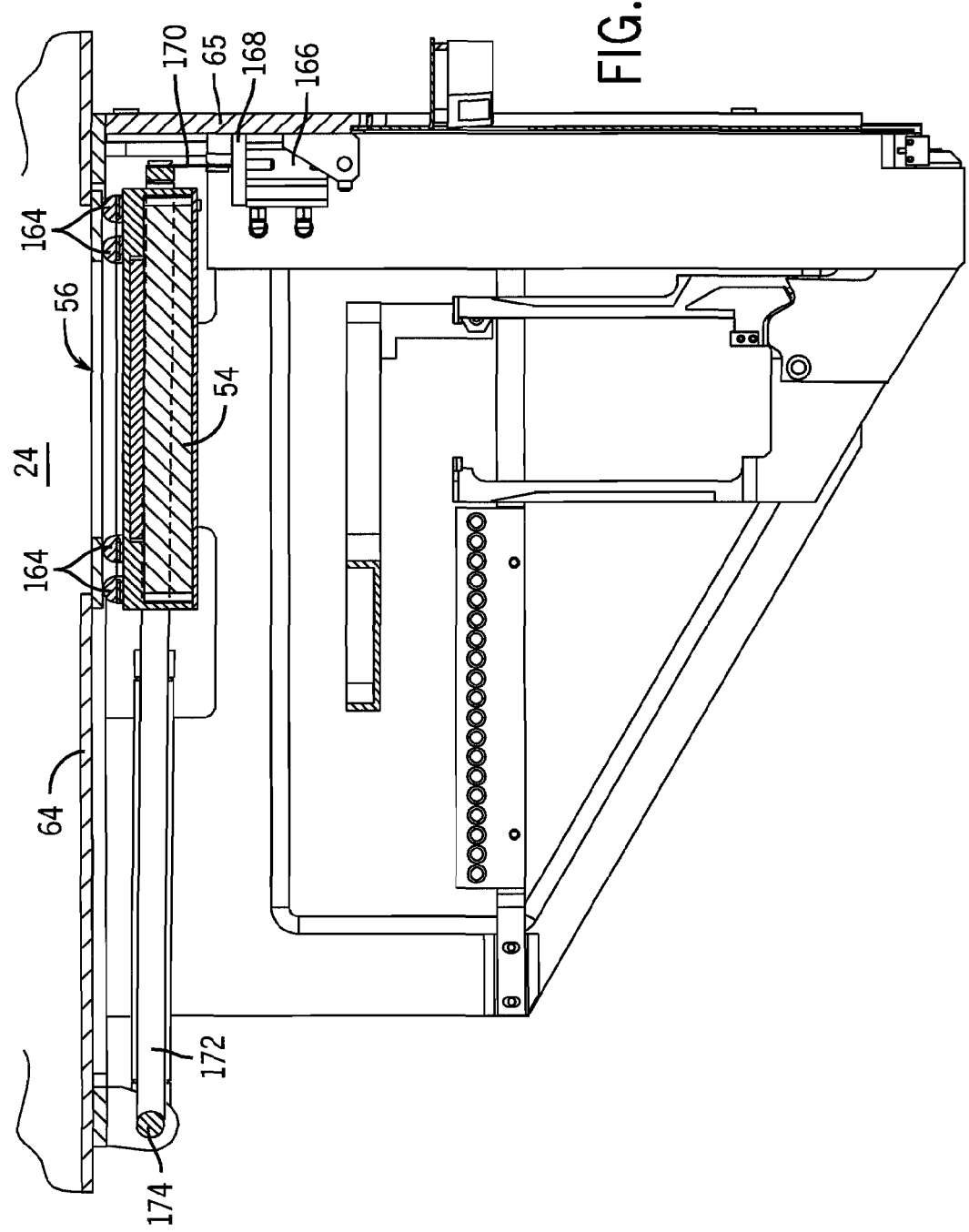
FIG. 10 is a downward looking sectional view of the tube picking mechanism taken at a location below the level of the gripper head assembly.
Figure 11:
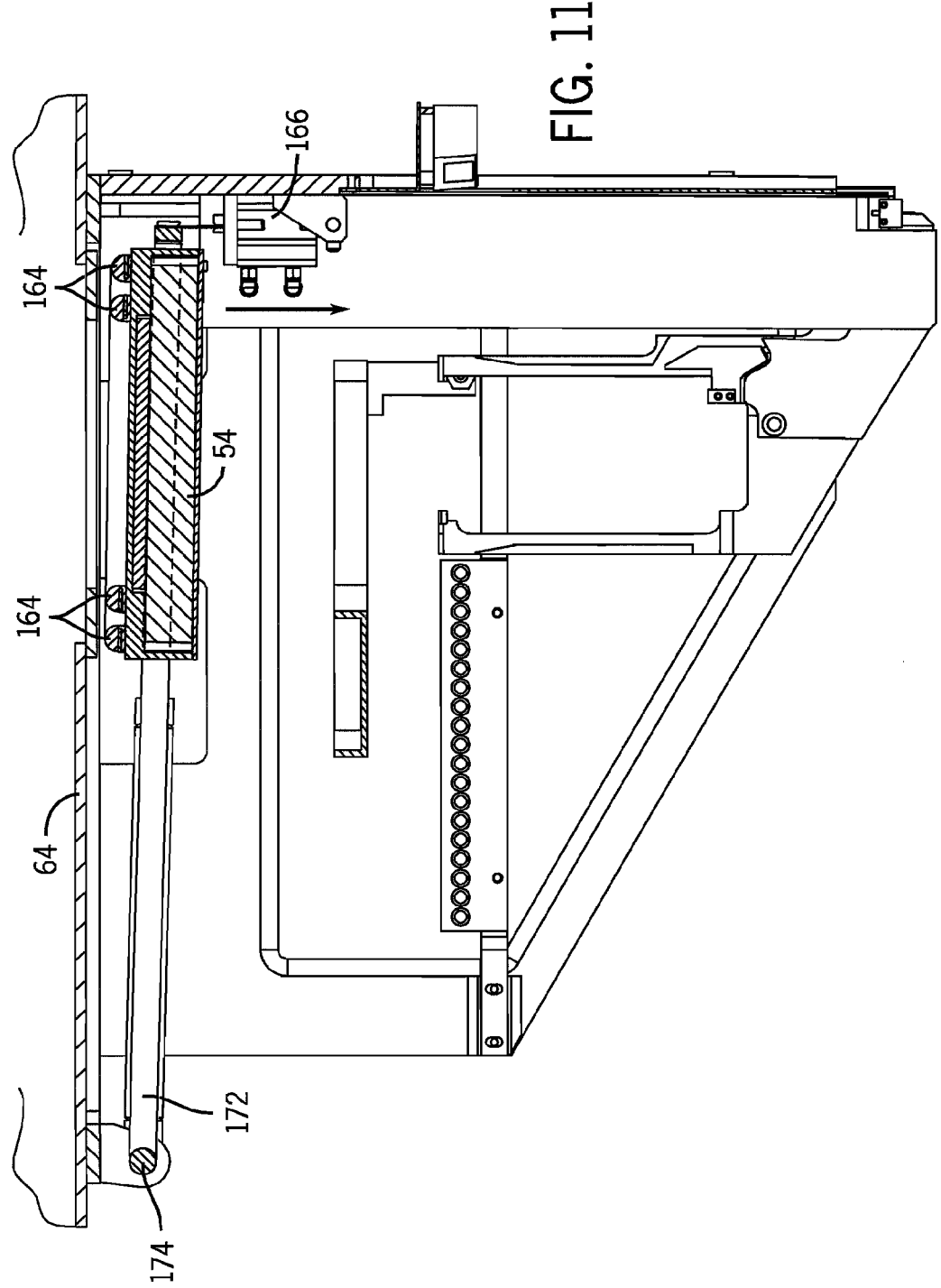
FIG. 11 is a view similar to FIG. 10 showing the shuttle door being popped open from a doorway between the tube picking chamber and the main freezer compartment.
Figure 12:
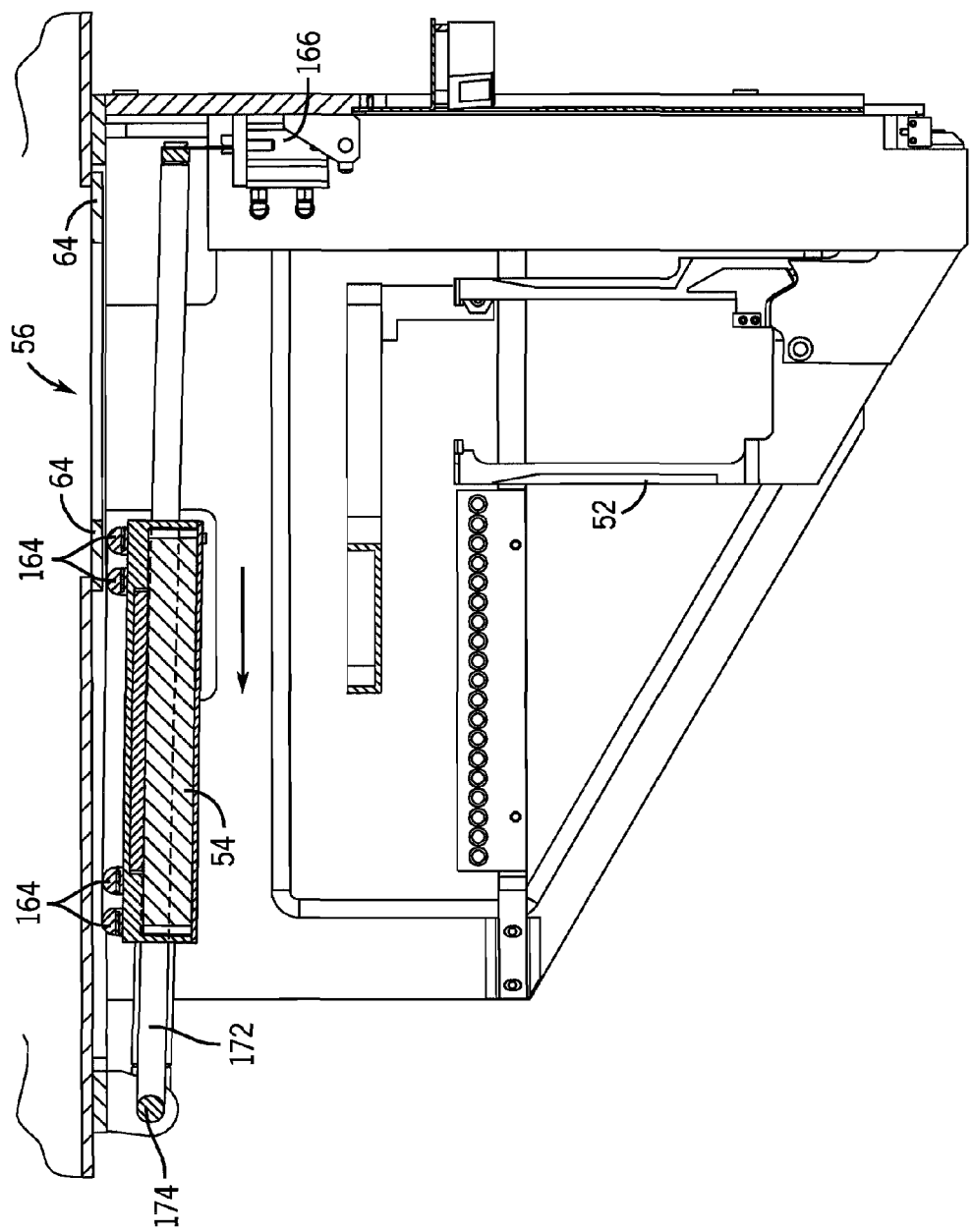
FIG. 12 is a view similar to FIGS. 10 and 11 showing the shuttle door being retracted away from the doorway to allow passage of a shuttle through the doorway.

FIGS. 10, 11 and 12 show the preferred operation of the shuttle door 54. The door 54 is an insulated door having a body preferably made of polyvinylchloride. The side of the door 54 facing the freezer compartment 24 includes a pair of resilient seals 164. The seals 164 compress against the frame 64 around the doorway 56. A double-acting, single rod air cylinder 166 is mounted to the frame 65 of the tube picking mechanism 32 by a bracket 168. The preferred air cylinder 166 has a stroke of 15 mm and a bore size of 25 mm. A piston for the air cylinder 166 is connected, via a piece of sheet metal 170, to the end of the door 54. The sheet metal connector piece 170 is somewhat flexible. The preferred air cylinder 166 provides 50 lbs. of force in either direction as it extends and retracts the connector 170 to open and close the door 54. The preferred air cylinder assembly also includes a biasing spring to keep the door 54 closed in case air pressure is lost to the system 10. The door 54 is mounted to a pair of guide rods 172. Referring briefly to FIG. 4, one guide rod 172 is attached to the upper portion of the door 54 while the other guide rod 172 is attached to the lower portion of the door 54. The door 54 is coupled to the guide rods 172 so that it is able to slide along the guide rods 172. The guide rods 172 are pivotally attached along a hinged vertical rod support 174. Still referring to FIG. 4, a pair of pneumatically operated cylinders 176 (double-acting cylinder preferably having a stroke of about 6.5 inches) are also attached to the hinged vertical support rod 174 at one end, and to the door 54 at the other end. After the piston for air cylinder 166 opens the door 54, the pivotally mounted air cylinders 176 retract the door 54 away from the doorway 56 along the guide rods 172. Referring again to FIGS. 10-12, FIG. 10 shows the door 54 in a closed position with the seals 164 being pressed against the frame 64 around the doorway 56. FIG. 11 illustrates the piston for the air pressure cylinder 166 pulling the door 54 away from the frame 64 in order to release the seal between the seals 164 on the door 54 and the frame 64. FIG. 12 shows the door 54 in the retracted position away from the doorway 56 in order to allow the shuttle 52 to move through the doorway 56. As mentioned, the pivotally mounted air cylinders 176 provide the power to move the door 54 along the guide rolls 172. When it is time to close the door 54, the pivotally mounted air cylinders 176 push the door 54 along the guide rolls 172 in front of the doorway 56, and the piston for the air cylinder 166 pushes the door 54 shut so that the seals 164 press against the frame 64 of the tube picking chamber 30.

The construction and operation of the shuttle 52 is shown in FIGS. 13A, 13B, 14A and 14B. In FIG. 13A, the shuttle 52 is fully extended into the freezer compartment 24, and a tube storage rack 176 has been placed in the shuttle 52 at designated location 50, FIG. 3. In FIG. 13A, the shuttle 52 is shown in the fully retracted position (within the tube picking chamber 30) in phantom. Referring to FIG. 13B, the shuttle 52 includes a pair of arms 178, 180 that extend along the y-axis. Each of the arms 178, 180 includes a horizontal base surface 182, 184 which support the tube rack 176. There is an opening between the base surfaces 184, 182 on the arms 178, 180 which allows access by the presenter push pin 98 to receptacles 186 in the tube rack 176 from underneath the shuttle 52. While the opening is covered by the tube rack 176 in the view shown in FIG. 13B, the outline of the base surfaces 182, 184 is shown in phantom to the extent it resides underneath the tube rack 176. Each shuttle arm 178, 180 also includes a vertical wall 188, 190 which extends upward from the respective base 182, 184. The inside surface of wall 190 serves as an x-axis referencing plane which is used to locate the precise location of the tube rack 176, as will be discussed in more detail with respect to FIG. 14B. The distal ends of the arms 178, 180 each include a stub wall 192, 194 which is perpendicular to the y-axis. The stub walls 192, 194 serve as a y-axis referencing plane which will be described in more detail with respect to FIG. 14B. The distal end of arm 190 also includes a z-axis clamp 196. The z-axis clamp 196 is designed to fit over the lip 198 on the outer wall of an SBS standard tube rack 176, and will also be discussed again with respect to FIG. 14B.

When the shuttle 52 receives the tube rack 176 at the designated location 50 in the freezer compartment 24, the tube rack 176 fits relatively loosely within the shuttle tray 52 except that the proximal end 200 of the tube rack 176 abuts a backstop 202 on the shuttle 52. The backstop 202 is a short vertical wall having a backstop surface that is perpendicular to movement along the y-axis. The backstop 202 is preferably located on the same side of the shuttle 52 as the z-axis clamp 196 on the arm 180, however, the backstop 202 is located at the proximal end of the shuttle whereas the z-axis clamp 196 on arm 180 is located at the distal end of the shuttle 52. The shuttle 52 also includes a clamping mechanism shown generally by reference arrows 204. The clamping mechanism 204 is generally located at the proximal end of the shuttle 52 on the side opposite the backstop 202 and the z-axis clamp 196 on arm 180. The clamping mechanism 204 includes a cam lever plate 206. The cam lever 206 is pivotally mounted to the body 208 of the shuttle 52 at a pivot axis 210. Preferably, the pivotable connection 210 comprises a plastic bearing in the cam lever plate 206 and an upwardly extending cylindrical stud connected to the body 208 of the shuttle 52. A cam follower 212 extends upward from an end of the cam lever 206. Referring briefly again to FIG. 13A, the cam follower 212 resides in a cam groove 214 that has been machined into the bottom surface of the y-axis horizontal shelf 216 located within the tube picking chamber 30. As can be seen in FIG. 13A, the shape of the cam groove 214 is selected so that the cam lever 206 rotates in the clockwise direction (i.e. to open the clamping mechanism 204) when the shuttle 52 is transported from the tube picking chamber 30 into the freezer compartment 24. On the other hand, the shape of the cam groove 214 causes the cam lever 206 to rotate counter-clockwise in order to close the clamping mechanism 204 when the shuttle 52 is retracted into the tube picking chamber 30.

A linear bearing block 218 for the y-axis rail is attached to the body 208 of the shuttle 52. The y-axis rail is shown in phantom in FIG. 13A, see reference number 220. The shuttle is driven along the y-axis rail 220 via stepper motor 222, FIG. 4. The stepper motor 222 includes an encoder 224. The stepper motor 222 drives a pulley and belt arrangement similar to the other axes, and the shuttle is clamped to the belt in a manner similar to that described above with respect to the stepper motors for the other axes.

Referring again to FIG. 13B, the clamping mechanism 204 includes a corner grabber 226. The corner grabber 226 is machined to have a 90° rack receiving edge 228. The corner grabber 226 includes a flange 230 containing an oversized hole (shown in phantom via reference number 232). A pin 234 on the cam lever 206 passes through the oversized hole 232 on the flange 230. The corner grabber 226 also includes a spring plunger 236 which is seated within the body of the corner grabber 226 and extends outward to contact the cam lever 206. The purpose of the spring plunger 236 is to maintain the corner grabber 226 in the cocked position, i.e. maintaining the rack receiving edge 228 square with the corner of the tube rack 176 located in the shuttle tray 52, whether the shuttle 52 is in the fully extended position as shown in FIG. 13B or the fully retracted position as shown in FIG. 14B. A second z-axis clamp 238 is attached to the corner grabber 226.

Referring now to FIGS. 14A and 14B, when the shuttle 52 receives a tube rack 176 from the designated location 50 in the freezer compartment 24 and transfers the rack 176 along the y-axis into the tube picking chamber 30, the shuttle clamping mechanism 204 clamps the tube rack 176 in a precise location on the shuttle 52. More specifically, as the cam lever 206 rotates counter-clockwise, the spring plunger 236 pushes on the corner grabber 226. As the corner grabber 226 is pushed, the rack receiving edge 228 engages a proximal corner of the tube rack 176. The corner grabber 226 continues to push the tube rack 176 on the shuttle 52 such that the rack 176 first engages the inside surface of vertical wall 190 on the opposing arm 180 in order to place the tube rack 176 at a precise location along the x-axis. The corner grabber 226 then continues to push the tube rack 176 towards the distal end of the opposite arm 180 and in particular into engagement with stub wall 194, as well as stub wall 192 on the near side arm 178. Pushing the tube rack 176 against the stub walls 194, 192 moves the tube rack 176 into a precise y-axis location with respect to the shuttle 52. When the corner grabber 226 is fully engaged, the z-axis clamp 196 on the arm 180 engages one end of the tube rack 176 whereas the z-axis clamp 238 on the corner grabber 226 engages the other end of the tube rack 176. Thus, when the shuttle 52 is located within the tube picking chamber 30, the tube rack 176 is fixed in a precise location with respect to the x-axis and z-axis location, and its relative location along the y-axis with respect on the shuttle 52 is also fixed.

When the shuttle 52 transports a rack 176 to the designated location 50 in the freezer compartment 24, the pin 234 on the cam follower 206 pulls on the corner grabber 226 to loosen the grip on the rack 176. Once the shuttle tray 52 is in the designated location 50, the robot 48 slightly pushes the tube rack 176 in order to release the tube rack 176 from the z-axis clamp 196 at the distal end of arm 194. The robot 48 may then remove the tube rack 176 from the shuttle tray 52.

Figure 15:
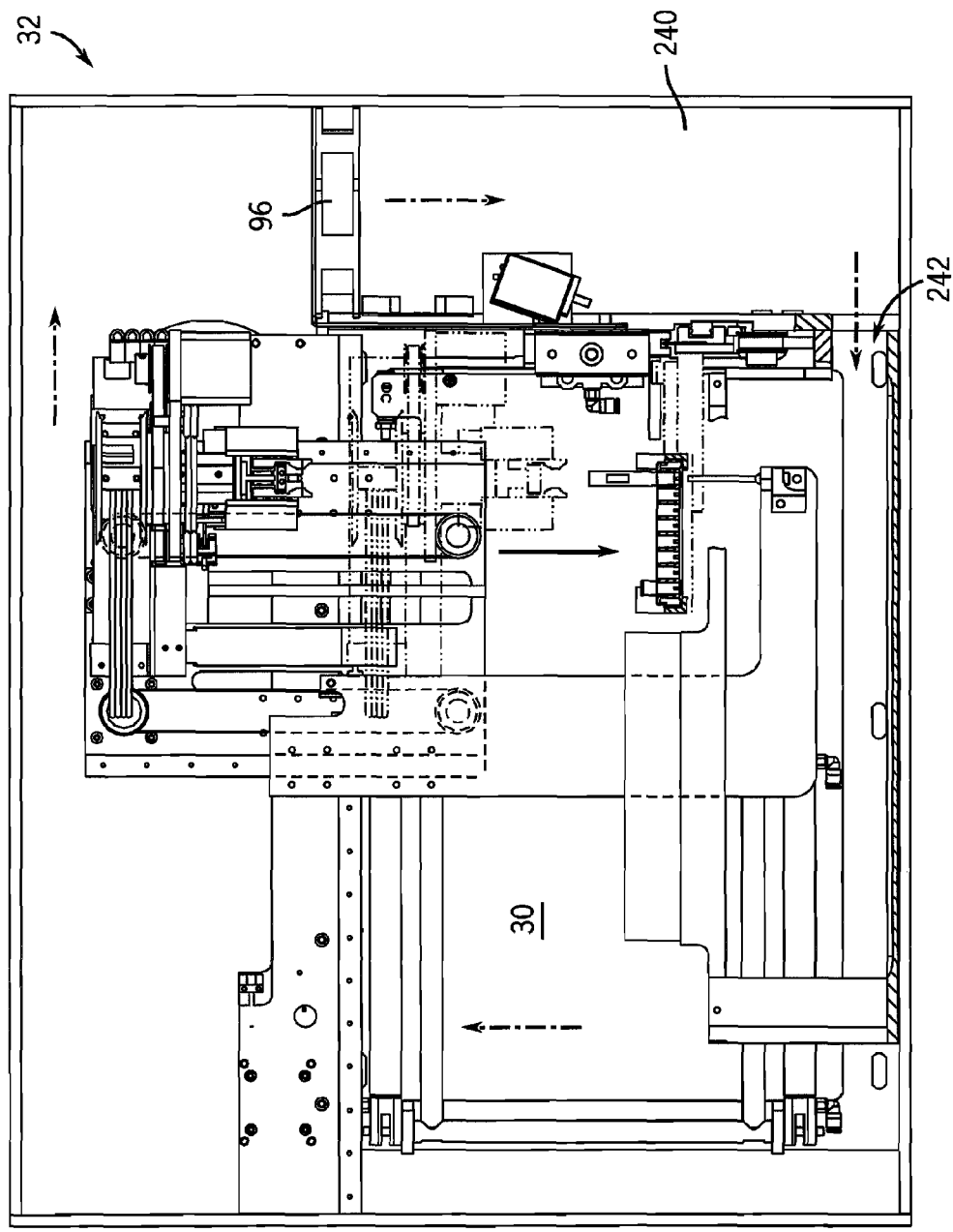
FIG. 15 is an elevational view of the preferred tube picking mechanism residing in the tube picking chamber, showing the preferred manner of continuously circulating air throughout the tube picking chamber.

Referring now to FIG. 15, as mentioned, the tube picking mechanism 32 includes a circulation fan 94. The preferred circulation fan 96 is a 24V DC fan having an output of 60 a cubic feet per minute. The tube picking mechanism 32 is designed with a plenum 240 below the fan 96. The fan 96 blows circulation air through the plenum 240. The circulating air passes through an opening 242 at the bottom of the plenum 240 into the main compartment of the tube picking chamber 30. The circulating air passes through the main compartment of the tube picking chamber 30 and up and over the tube picking mechanism 32, as indicated by the dashed arrows in FIG. 15. The air is then drawn into the fan 96 and recirculated. In accordance with a preferred embodiment of the invention, the circulation fan 96 remains "on" from the moment that a signal is received to prepare the tube picking chamber 30 for picking tubes until the tube picking process is terminated. Another fan (not shown in the drawings), namely a cool down fan, is located within the tube picking chamber 30 and blows air out the open doorway 56 during the initial cool down process. This fan is preferably the same size as the circulation fan 96. It has been found that blowing air out of the door accelerates the initial cool down process and therefore lessens the time in which the door 54 between the tube picking chamber 30 and the freezer compartment 24 needs to be open for initial cool down. As described in the above-incorporated copending patent application, the tube picking chamber 30 is passively cooled by opening and closing the door 54 between the tube picking chamber 30 and the freezer compartment 24. Initially, as mentioned, dry gas is blown into the tube picking chamber 30 while the door 54 is closed. When the relative humidity within the chamber 30 reaches a predetermined level such as 2% or less, the door 54 is then opened to cool the tube picking chamber 30. In accordance with the present invention, the cool down fan blows air from the tube picking chamber 30 through the doorway 56 during the initial cool down period. The temperature sensor within the tube picking chamber 30 monitors the temperature, and closes the door when the temperature reaches −20° C., or some other designated temperature. The circulation fan 96 continuously circulates air throughout the tube picking chamber 30 both during cool down and during the operation of the tube picking mechanism 32. When the temperature within the tube picking chamber 30 rises to another preselected level, preferably −15° C., the door 54 is opened or partially opened in order to passively re-cool the tube picking chamber 30 to −20° C., at which time the door 54 is closed.

Details of the tube picking process are now explained with respect to FIGS. 16-18. In FIG. 16, the presenter push pin 98 is shown pushing on the bottom of storage tube 244 to lift the storage tube 244 slightly from the receptacle in the storage tube rack 176. Preferably, the presenter push pin 98 pushes the tube 244 upward a distance on the order of ¼ of an inch, although this preferred distance may vary depending on the size of tubes and racks for which the system is designed. Importantly, the tube 244 is raised above the height of the adjacent tubes in the rack 176 so that the gripper fingers 126 on the gripper head 58 can access the sides of the tube 244 near its top. FIG. 17 shows the gripper fingers 126 closing on the sidewalls of the storage tube 244. FIG. 18 shows the gripper head 58 moving upward vertically along the z-axis in order to lift the tube 244 from the storage rack 176.

Figure 19:
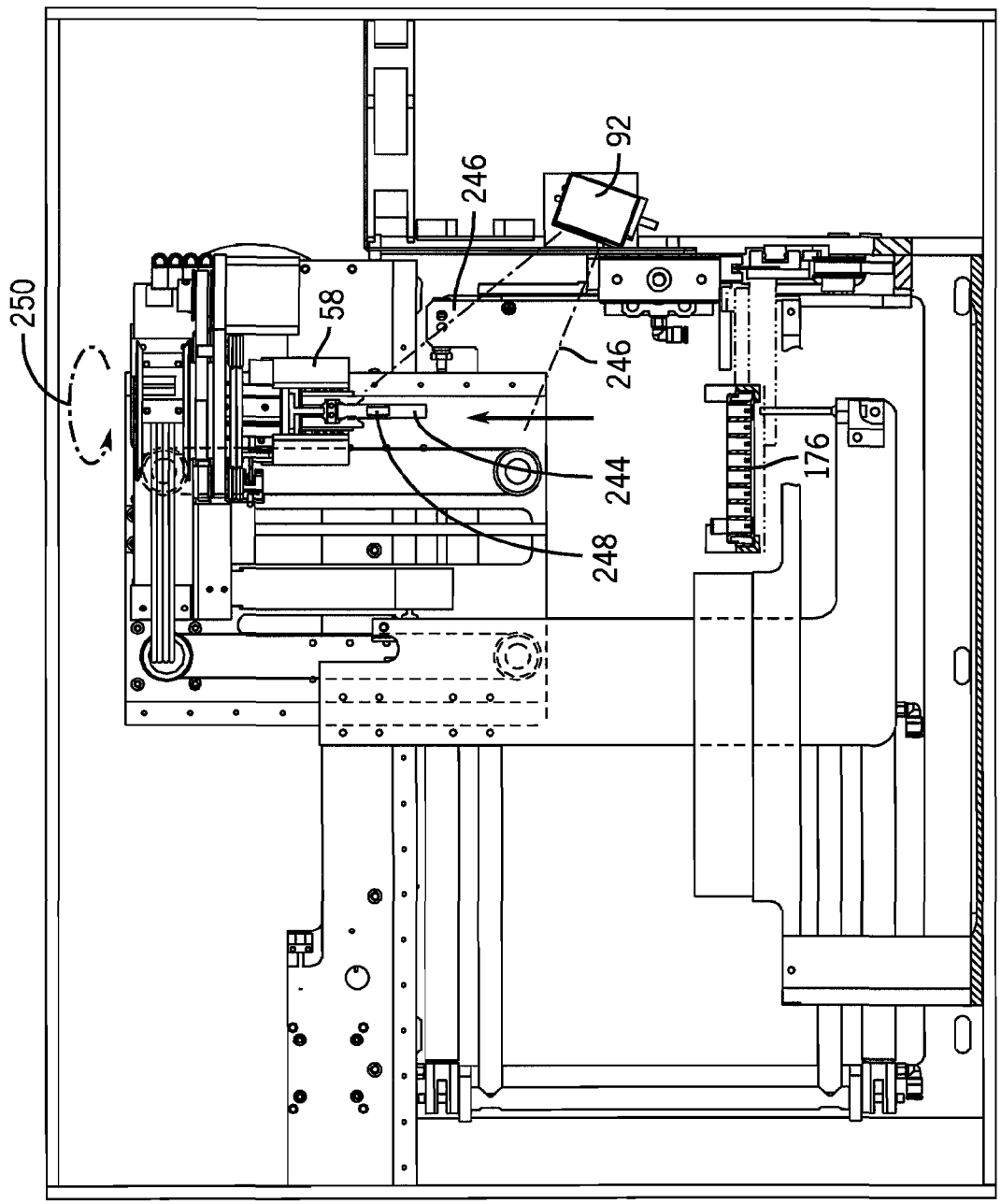
FIG. 19 is a front elevational view illustrating the field of view of a one-dimensional barcode reader within the tube picking chamber.

Referring now to FIG. 19, the gripper head 58 lifts the storage tube 244 vertically along the z-axis into the field of view of the one-dimensional bar code reader 92. The field of view of the one-dimensional bar code reader 92 is indicated in FIG. 9 by dashed lines 246. A one-dimensional bar code label 248 with information identifying the source of the biological or chemical sample is adhered to a sidewall of the tube 244. The gripper head 58 rotates as indicated by arrow 250 to bring the one-dimensional bar code label 248 into an orientation in which the bar code 248 faces the one-dimensional bar code reader 92. Once this occurs, the bar code reader 92 reads the bar code 248 automatically. The tube picking mechanism 32 can be used to read all of the tubes 244 in a storage plate 176, for example, when the storage rack 176 is initially entered into the automated, low temperature storage and retrieval system 10. Once the tubes 244 are read, the system control system can keep track of the precise location within the freezer compartment of each of the tubes 244 and each of the storage racks 176. Alternatively, the one-dimensional bar code reader 92 can be used to confirm the identity of the tubes 244 being picked from a storage plate 176 prior to being extracted from the system 10.

Figure 20:
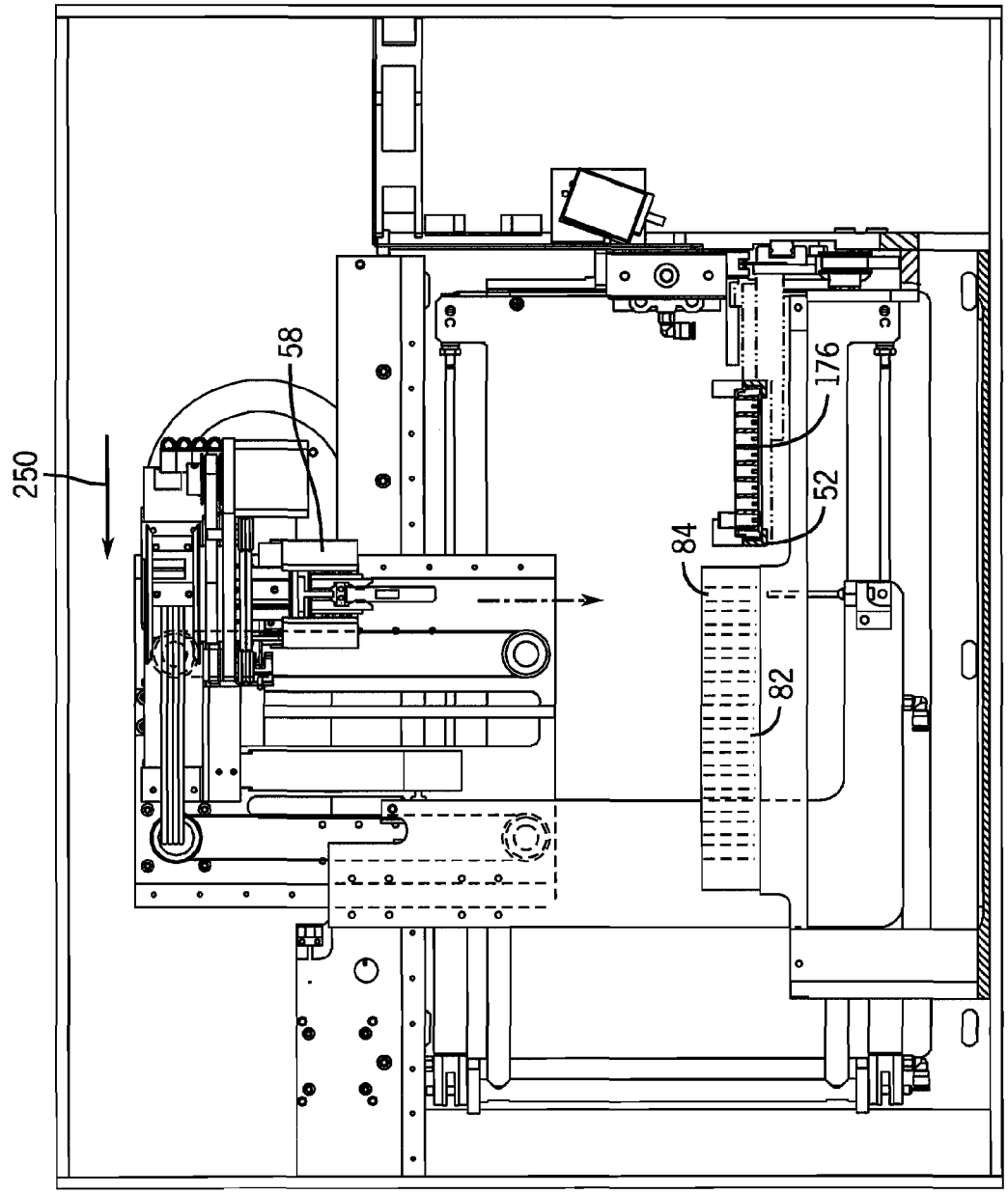
FIG. 20 is a front elevational view showing the tube picking mechanism transferring a picked tube from a source rack to a cache located within the tube picking chamber as in accordance with the preferred embodiment of the invention.
Figure 21:
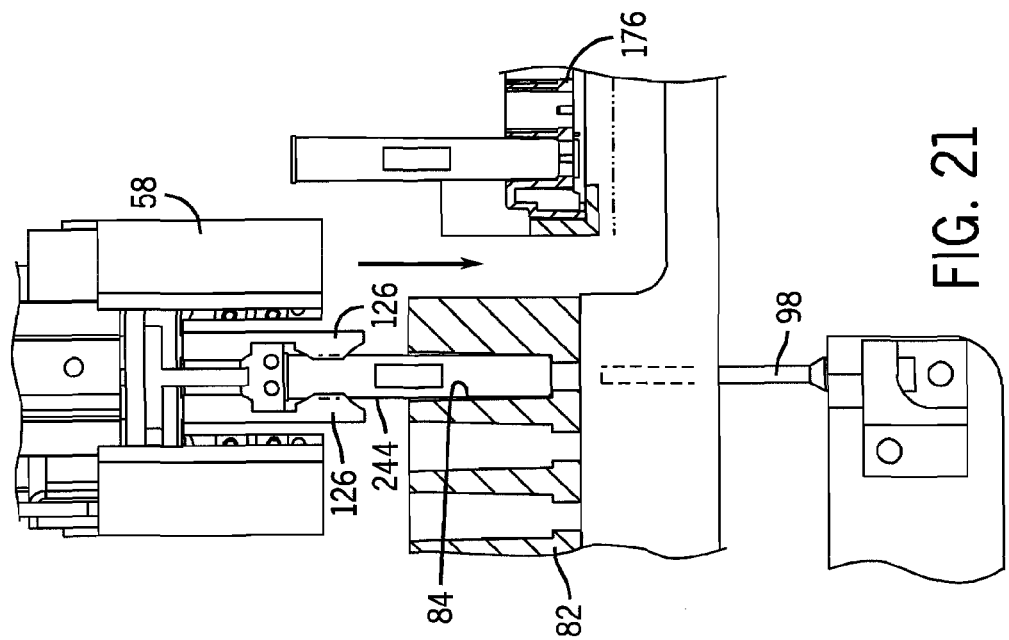
FIGS. 21 and 22 are detailed views schematically illustrating the placement of a picked storage tube into the cache located in the tube picking chamber.
Figure 22:
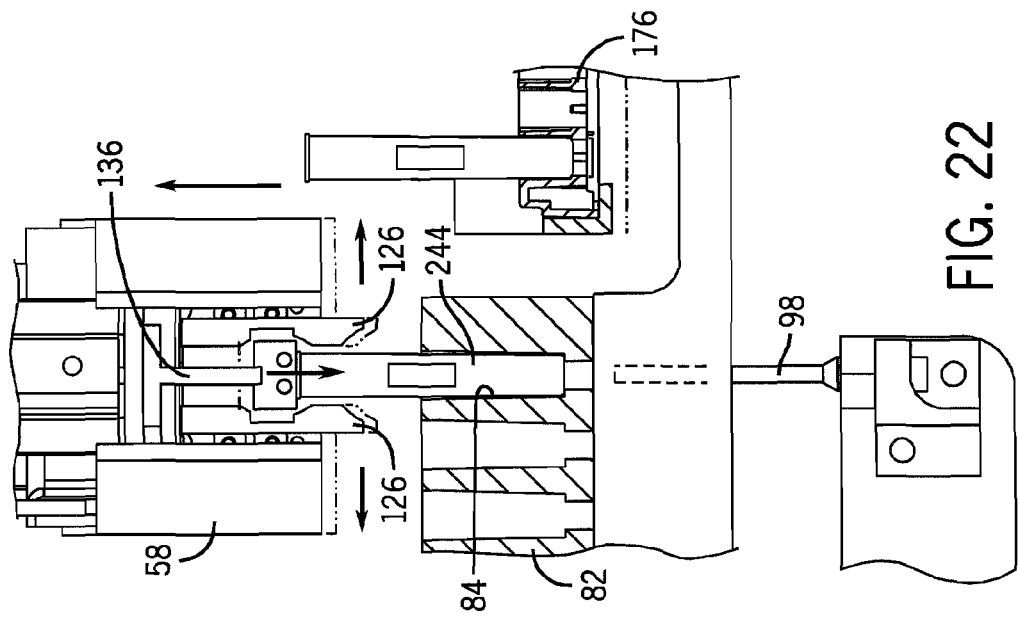

FIG. 20 illustrates a gripper head 58 moving along the x-axis, see arrow 250, to transfer a picked tube 244 from a storage plate 176 located in the shuttle 52 to a receptacle 84 in the cache 82. FIGS. 21 and 22 show a more detailed view of the gripper head 58 placing the tube 244 into the receptacle 84 in the cache 82. Note that the presenter push pin 98 is not raised to engage the storage tube 244 when placing the tube 244 in the receptacle 84 in the cache 82. Rather, as shown in FIG. 22, the shucker 136 on the gripper head 58 pushes downward on the tube 244 to secure the tube 244 within the receptacle 84.

Note that tube picking mechanism 32 operates in a similar manner to pick tubes from the cache 82, as explained above with respect to picking tubes 244 from a tube rack 176. On the other hand, the picking mechanism 32 operates in a similar manner to deposit a picked tube being transferred from the cache 82 to a destination rack 176, as explained above with respect to temporarily depositing a tube 244 into a receptacle in the cache 82.

Many of the components in the preferred embodiment of the invention are machined from aluminum such as most of the shuttle components 52, the cache 82 and the gripper fingers 126. The gripper fingers 126 and the cache 82, as mentioned, are custom-made to the size of the tubes that the system is designed to handle.

The preferred embodiment of the invention has been described herein with respect to use with an ultra-low temperature (−80° C.), automatic storage and retrieval system. However, many of the features described herein may be useful in storage systems that store samples at freezing temperatures above the ultra-low temperature range. For example, certain features of the invention, for example the construction and operation of the shuttle and the clamping mechanism, or the rotating gripper head which enables the use of a one-dimensional bar code reader, may be useful in other systems. Those skilled in the art should appreciate that these features, among others, while useful in connection with tube picking mechanisms located in a tube picking chamber adjacent an ultra-low temperature (−80° C.) freezer compartment, are also useful in other applications as well.

We claim:

1. An automated, ultra-low temperature sample storage and retrieval system comprising:
   a freezer body having an ultra-low temperature, insulated compartment that is maintained at an ultra-low temperature from about −50° C. to −90° C. under normal operating conditions when biological or chemical samples are being stored in the ultra-low temperature compartment;
   at least one freezer rack having trays for storing sample storage containers holding biological or chemical samples, wherein at least some of the sample storage containers are tube racks which hold sealed tubes containing biological or chemical samples;
   a robot located within the ultra-low temperature freezer compartment for transporting storage sample containers within the freezer compartment;
   an access module for introducing sample storage containers into the ultra-low temperature freezer compartment and for retrieving storage containers from the ultra-low temperature freezer compartment; and
   a tube picking mechanism located within a tube picking chamber, there being a shuttle door which provides access when open between the tube picking chamber and the ultra-low temperature storage compartment within the freezer, the tube picking mechanism comprising:
      a shuttle for moving tube storage racks through the shuttle door from the ultra-low temperature freezer compartment into the tube picking chamber and vice versa;
      a tube gripper head having a pair of fingers that is able to grip and lift a single tube from a receptacle in a tube rack located on the shuttle; and
      a cache having storage tube receptacles located within the tube picking chamber for temporarily holding a plurality of storage tubes within the tube picking chamber.

2. A system as recited in claim 1 wherein the shuttle includes:
   a shuttle tray having a clamping mechanism for holding an SBS footprint tube rack; and
   a presenter push pin which can be moved in a horizontal direction and a vertical direction, the presenter push pin being located below the shuttle tray and aligned with the gripper head along a vertical axis so that sufficient upward vertical movement of the presenter push pin can push on a bottom of a storage tube held in a tube receptacle in a tube rack clamped in the shuttle tray to slightly raise the storage tube above the height of the other tubes in the rack and facilitate lifting of the storage tube from the receptacle in the tube rack by the gripper head.

3. A system as recited in claim 1 wherein the shuttle moves in a first horizontal direction and the shuttle tray comprises:
   a pair of arms extending generally in the direction that the shuttle moves with an opening between the arms, wherein each arm has a base for supporting a tube rack in the shuttle tray and vertical wall extending up from the base;
   a backstop;
   a y-axis referencing wall and a z-axis clamp located at a distal end of a first one of the arms; and
   a clamping mechanism located at a proximal end of the other arm, the clamping mechanism pushing a tube rack into engagement with the y-axis referencing wall and the z-axis clamp and the adjacent vertical wall which serves as an x-axis on the first arm when the shuttle is located within the tube picking chamber.

4. A system as recited in claim 3 further comprising a cam follower that drives a pivotable cam mechanism to open and close the clamping mechanism, the cam follower engaging and being driven by a groove located within the tube picking chamber.

5. A system as recited in claim 1 further comprising a y-axis linear drive mechanism located within the tube picking chamber which is mounted to the frame of the tube picking mechanism and moves the shuttle horizontally along a y-axis such that the shuttle resides within the freezer compartment when the y-axis linear drive mechanism is fully extended and resides within the tube picking chamber when the y-axis linear drive mechanism is fully retracted.

6. A tube picking mechanism comprising:
   a shuttle for moving tube racks through an opened shuttle doorway into and out of a tube picking chamber;
   a tube gripper head having a pair of gripper head fingers that are able to grip and lift a single tube from a receptacle in a tube rack and a shucker for transferring the picked tube from the gripper fingers when the gripper fingers release, wherein the gripper head is movable vertically along a z-axis and is also rotatable about the z-axis; and
   a one-dimensional bar code reader for identifying and reading a bar code on a sidewall of a storage tube picked and lifted by the gripper fingers.

7. A tube picking mechanism as recited in claim 6 further comprising:
   a bearing mechanism for rotatably mounting the gripper head to a carriage head; and
   a gripper head motor for rotating the gripper head about the z-axis with respect to the carriage head.

8. A tube picking mechanism as recited in claim 7 further comprising a z-axis linear drive mechanism that moves the carriage head vertically along the z-axis.

9. A system as recited in claim 8 wherein movement of the gripper head fingers and the shucker on the gripper head assembly are pneumatically powered, and air supply tubing wraps or unwraps around the gripper head as the gripper head is rotated by the gripper head motor depending on the direction of rotation.

10. A system as recited in claim 8 wherein the z-axis linear drive mechanism is mounted to a z-axis plate and the system further comprises:
    a frame;
    an x-axis linear drive mechanism mounted to the frame that moves the z-axis plate horizontally along an x-axis which is substantially perpendicular to the z-axis; and
    a y-axis linear drive mechanism mounted to the frame that moves the shuttle horizontally along the y-axis which is substantially perpendicular to both the x-axis and the y-axis.

11. In an automated, ultra-low temperature sample storage and retrieval system having a freezer body with an insulated compartment that is maintained at an ultra-low temperature from about −50° C. to −90° C. under normal operating conditions, at least one storage rack having trays for storing storage containers holding biological or chemical samples in the freezer compartment, a robot located within the freezer compartment for transporting storage sample containers within the freezer compartment, an access module for introducing sample storage containers into the ultra-low temperature freezer chamber and for retrieving containers from the freezer compartment, and a tube picking mechanism located within a tube picking compartment that is adjacent to and separate from the ultra-low temperature freezer compartment, a method of cooling and maintaining an appropriate temperature in the tube picking compartment comprising the steps of:

receiving a signal to prepare the tube picking chamber prior to using the tube picking mechanism;

opening a door between the tube picking chamber and the freezer compartment in order to allow ultra-low temperature air from the freezer compartment into the tube picking chamber for initial cool down;

blowing air from the tube picking chamber through the open door into the freezer compartment with a cool down fan;

closing the door when the temperature within the tube picking chamber reaches a first predetermined temperature, and terminating operation of the cool down fan until it is necessary to prepare the tube picking chamber for another initial cool down;

opening the door when the temperature within the tube picking chamber rises to a second predetermined temperature in order to cool the chamber without blowing air from the tube picking chamber through the open door into the freezer compartment with the cool down fan; and continuing to close and open the door in order to maintain the temperature within the tube picking chamber within the predetermined temperature range.

12. A method as recited in claim 11 wherein minimum and maximum values for the predetermined temperature range are selected to be no less than −20° and no greater than −15° C.

13. In an automated, ultra-low temperature sample storage and retrieval system having a freezer body with an insulated compartment that is maintained at an ultra-low temperature from about −50° C. to −90° C. under normal operating conditions, at least one storage rack having trays for storing storage containers holding biological or chemical samples in the freezer compartment, a robot located within the freezer compartment for transporting storage sample containers within the freezer compartment, an access module for introducing sample storage containers into the ultra-low temperature freezer chamber and for retrieving containers from the freezer compartment, and a tube picking mechanism located within a tube picking compartment that is adjacent to and separate from the ultra-low temperature freezer compartment, a method of cooling and maintaining an appropriate temperature in the tube picking compartment comprising the steps of:

receiving a signal to prepare the tube picking chamber prior to using the tube picking mechanism;

circulating air throughout the tube picking chamber with a circulation fan;

opening a door between the tube picking chamber and the freezer compartment in order to allow ultra low temperature air from the freezer compartment into the tube picking chamber while the circulation fan is circulating air throughout the tube picking chamber;

closing the door when the temperature within the tube picking chamber reaches a first predetermined temperature, and continuing to circulate air throughout the tube picking chamber with the circulation fan;

opening the door when the temperature within the tube picking chamber rises to a second predetermined temperature and continuing to circulate air throughout the tube picking chamber with the circulation fan; and continuing to close and open the door in order to maintain the temperature within the tube picking chamber within a predetermined temperature range.

14. A method as recited in claim 13 wherein during initial cool down, a cool down fan blows air from the tube picking chamber through the open door into the freezer compartment.

15. A method as recited in claim 14 further comprising the step of:

receiving a signal to cease operation of the tube picking mechanism;

closing the door when the operation of the tube picking mechanism has ceased; and terminating operation of the first fan once the operation of the tube picking mechanism has ceased.

16. A method of identifying one or more sample storage tubes containing a biological or chemical sample in an automated storage and retrieval system, the method comprising the steps of:

shuttling tube racks into a tube picking chamber one at a time, wherein the tube racks hold sealed tubes containing biological or chemical samples and at least some of the sealed tubes have a one-dimensional bar code on a sidewall of the tube for identifying the contents within the respective tube;

using a tube picking mechanism to pick individual storage tubes from each respective tube rack when it is located within the tube picking chamber;

presenting the picked tube within the field of view of a one-dimensional bar code reader located within the tube picking chamber;

using the tube picking mechanism to move and rotate the picked tube to facilitate identification and reading of a one-dimensional bar code located on a sidewall of the picked tube.

17. A method as recited in claim 16 further comprising the step of:

replacing the picked tube in the same receptacle in the same tube rack from which the respective tube was picked.

18. A method as recited in claim 16 further comprising the step of:

placing the picked tube within a receptacle in a cache located within the tube picking chamber once the tube has been identified.

19. A method as recited in claim 16 further comprising the step of:

scanning the bottom of storage tubes in tube racks for two-dimensional bar codes when introducing the tube racks through an access module into the freezer compartment; and further wherein selected tubes are scanned for one-dimensional bar codes on a sidewall of the tubes only when a two-dimensional bar code is not present on the tube.

20. In an automated, ultra-low temperature sample storage and retrieval system having a freezer body with an insulated compartment that is maintained at an ultra-low temperature from about −50° C. to −90° C. under normal operating conditions, at least one storage rack in the freezer compartment having trays for tube racks holding biological or chemical samples in sample storage tubes, a robot located within the freezer compartment for transporting tube racks within the freezer compartment, an access module for introducing sample storage containers into the ultra-low temperature freezer compartment and for retrieving containers from the freezer compartment, and a tube picking mechanism located within the tube picking chamber that is adjacent to and separate from the ultra-low temperature freezer compartment, a method of retrieving one or more sample storage tubes for retrieval from the system, the method comprising the steps of:

shuttling one or more source racks one at a time from the ultra-low temperature freezer compartment into the tube picking chamber;

picking at least one selected storage tube from each source rack shuttled into the tube picking chamber;

placing the pick storage tubes in one of a plurality of receptacles of a cache located within the tube picking chamber;

returning each respective source rack to the ultra-low temperature freezer compartment when the selected tubes have been picked from the source rack and placed in the cache;

providing an destination rack intended to be removed from the system through the access module;

shuttling the destination rack into the tube picking chamber and loading tubes from the cache into the destination rack;

returning the destination rack into the freezer compartment; and removing the destination rack from the freezer compartment through the access module.

21. A method as recited in claim 20 wherein a shuttle door is located between the tube picking chamber and the freezer compartment and the method further comprises the steps of:

closing the shuttle door whenever a tube rack is located in the tube picking chamber, unless it is necessary to cool the tube picking chamber.

22. A method as recited in claim 20 wherein the destination rack is shuttled into the tube picking chamber to load selected storage tubes from the cache several times prior to removing the destination rack from the system through the access module.

* * * * *